US006358968B1

(12) United States Patent
Remiszewski et al.

(10) Patent No.: US 6,358,968 B1
(45) Date of Patent: *Mar. 19, 2002

(54) N-SUBSTITUTED UREA INHIBITORS OF FARNESYL-PROTEIN TRANSFERASE

(75) Inventors: Stacy W. Remiszewski, Washington Township, Bergen County; Alan K. Mallams, Hackettstown, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,375

(22) Filed: Jan. 14, 2000

Related U.S. Application Data

(63) Continuation of application No. 09/094,682, filed on Jun. 15, 1998, now abandoned.
(60) Provisional application No. 60/049,959, filed on Jun. 17, 1997.

(51) Int. Cl.[7] .................. A61K 31/4545; C07D 401/14; A61P 35/00
(52) U.S. Cl. .......................................... 514/290; 546/93
(58) Field of Search .............................. 514/290; 546/93

(56) References Cited

U.S. PATENT DOCUMENTS

| 5,661,152 A | * | 8/1997 | Bishop | 514/254 |
| 5,696,121 A | | 12/1997 | Bishop | 514/254 |
| 5,719,148 A | * | 2/1998 | Bishop | 514/228.2 |

FOREIGN PATENT DOCUMENTS

| WO | WO 95 10516 A | 4/1995 |
| WO | WO 96 30363 A | 10/1996 |
| WO | WO 96 31478 A | 10/1996 |
| WO | WO 97 23478 A | 7/1997 |
| WO | WO 98 11091 A | 3/1998 |
| WO | WO 98 11099 A | 3/1998 |

OTHER PUBLICATIONS

Khosravi–Far R et al. Cell Growth & Differentiation. 3, 461–9, Jul. 1992.*
King, F.D., Medicinal Chemistry. Principles and Practice. The Royal Society of Chemsitry. Thomas Graham House, The Science Park, pp. 206–209.
Roya Khosravi–Far et al., Protein Prenylation: Key to Ras Function and Cancer Intervention?, Cell Growth & Differentiation, vol. 3, (Jul. 1992), pp. 461–469.
Bishop, W. R., et al., Novel Tricyclic Inhibitors of Farnesyl Protein Transferase. Biochemical Characterization and Inhibition of Ras Modification in Transfected Cos Cells. The Journal of Biological Chemistry, vol. 270, No. 5; Dec. 22, 1995: 30611–30618.
Njoroge, F.G., et al., Novel Tricyclic Aminoacetyl and Sulfonamide Inhibitors of Ras Farnesyl Protein Transferase. Bioorganic & Medical Chemistry Letters, vol. 6. No. 24, pp. 2977–2981, 1996.

* cited by examiner

*Primary Examiner*—Evelyn Mei Huang
(74) *Attorney, Agent, or Firm*—Margaret M. Albanese; Henry C. Jeanette; Joseph T. Majka

(57) ABSTRACT

Novel halo-N-substituted urea compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel halo-N-substituted urea compound to a biological system. In particular, the method inhibits the abnormal growth of cells in a mammals such as a human.

13 Claims, No Drawings

N-SUBSTITUTED UREA INHIBITORS OF FARNESYL-PROTEIN TRANSFERASE

REFERENCE TO RELATED APPLICATIONS

This application is a continuation of application Ser. No. 09/094,682 filed Jun. 15, 1998, now abandoned, which application claims the benefit of U.S. Provisional Application Serial No. 60/049,959 filed Jun. 17, 1997.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

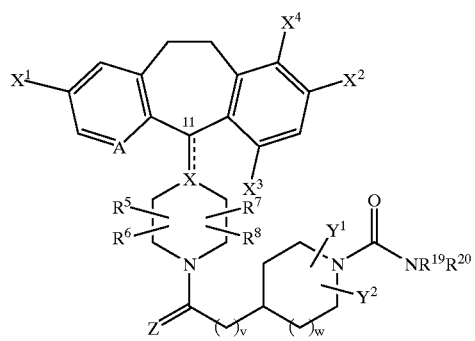

(1.0)

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$X^1$ and $X^2$ are independently selected from bromo or chloro, and $X^3$ and $X^4$ are independently selected from hydrogen, bromo or chloro provided that at least one of $X^3$ and $X^4$ is hydrogen;

$Y^1$ and $Y^2$ are independently selected from hydrogen or alkyl;

Z is =O or =S;

$R^5$, $R^6$, $R^7$ and $R^8$ each independently represents hydrogen, —$CF_3$, —$COR^{10}$, alkyl or aryl, and further wherein $R^5$ may be combined with $R^6$ to represent =O or =S and/or $R^7$ may be combined with $R^8$ to represent =O or =S;

$R^{10}$, $R^{19}$ and $R^{20}$ independently represent hydrogen, alkyl, alkoxy, aryl, aralkyl, heteroaryl, heteroarylalkyl, cycloalkyl, cycloalkylalkyl, heterocycloalkyl and heterocycloalkylalkyl, with the proviso that $R^{19}$ and $R^{20}$ are not both hydrogen;

v is zero, 1, 2 or 3; and w is zero or 1.

Preferably in compound (1.0), there is a single bond at carbon atom 11; X is CH; $R^5$, $R^6$, $R^7$ and $R^8$ are hydrogen; $X^1$, $X^2$ and $X^3$ are bromo or chloro and $X^4$ is hydrogen; Z is =O; v is 1; w is 1; $Y^1$ and $Y^2$ are hydrogen; and $R^{19}$ and $R^{20}$ are independently selected from hydrogen, alkyl, aryl and heterocycloalkyl with the proviso that $R^{19}$ and $R^{20}$ are not both hydrogen. When $R^{19}$ or $R^{20}$ is alkyl, optional substituents on the alkyl group may include —$OR^{10}$, alkoxy, —$OCOR^{10}$, —$CONR^{10}R^{12}$ or —$COOR^{10}$, wherein $R^{10}$ and $R^{12}$ are independently selected from hydrogen, alkyl or alkoxy. When $R^{19}$ or $R^{20}$ is aryl, an optional substituent on the aryl group may include alkoxy. When $R^{19}$ or $R^{20}$ is heterocycloalkyl, an optional substituent on the heterocycloalkyl group may include —$COOR^{10}$ wherein $R^{10}$ is hydrogen or alkyl. Preferred title compounds include those of Examples 3, 4, 6, 7, 11, 12 and 13, disclosed hereinafter.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells, prostate tumor cells, breast tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, prostate carcinoma and breast carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the N-substituted urea compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the N-substituted urea compounds (1.0).

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

M+—represents the molecular ion of the molecule in the mass spectrum;

MH+—represents the molecular ion plus hydrogen of the molecule in the mass spectrum;

Bu—represents butyl;

Et—represents ethyl;

Me—represents methyl;

Ph—represents phenyl;

benzotriazol-1-yloxy represents

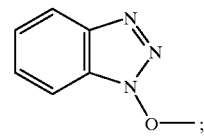

1-methyl-tetrazol-5-ylthio represents

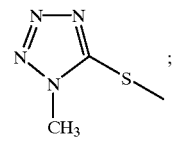

alkyl-(including the alkyl portions of alkoxy, alkylamino and dialkylamino)-represents straight and branched carbon chains and contains from one to twenty carbon atoms, preferably one to six carbon atoms; for example methyl, ethyl, propyl, iso-propyl, n-butyl, t-butyl, n-pentyl, isopentyl, hexyl and the like; wherein said alkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ can independently represent hydrogen, alkyl, alkoxy, aryl, aralkyl, heteroaryl, heteroarylalkyl, cycloalkyl, cycloalkylalkyl, heterocycloalkyl or heterocycloalkylalkyl;

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryloxy—represents an aryl group, as defined above, wherein said aryl group is covalently bonded to an adjacent structural element through an oxygen atom, for example, phenoxy, wherein said aryl group optionally can be fused with aryl, cycloalkyl, heteroaryl or heterocycloalkyl rings; and wherein any of the available substitutable carbon and nitrogen atoms in said aryloxy group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove.

Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

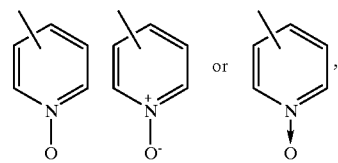

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove. Representative heterocycloalkyl groups can include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl,

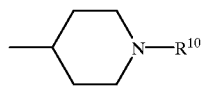

or

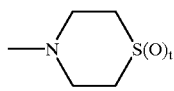

wherein R$^{10}$ is defined hereinbefore and t is 0, 1 or 2.

heterocycloalkalkyl—represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O); ethyl chloroformate (ClCO$_2$Et); and 1-(3-dimethylaminopropyl)-3-ethyl carbodiimide hydrochloride (DEC).

Reference to the position of the substituents X$^1$, X$^2$ and X$^3$ is based on the numbered ring structure:

(1.0)

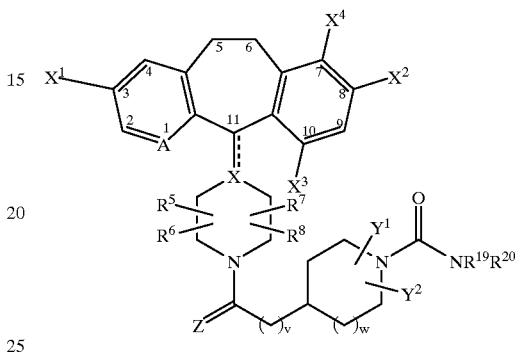

Certain compounds of the invention may exist in different stereoisomeric forms (e.g., enantiomers, diastereoisomers and atropisomers). The invention contemplates all such stereoisomers both in pure form and in mixture, including racemic mixtures. For example, the carbon atom at the C-11 position can be in the S or R stereoconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the present invention can be prepared according to the following Schemes I, II or III wherein A, X, X$^1$, X$^2$, X$^3$, X$^4$, Y$^1$, Y$^2$, Z, R$^5$, R$^6$, R$^7$ and R$^8$, R$^{19}$, R$^{20}$, v, w, the solid and dotted lines are as defined hereinbefore.

Scheme I

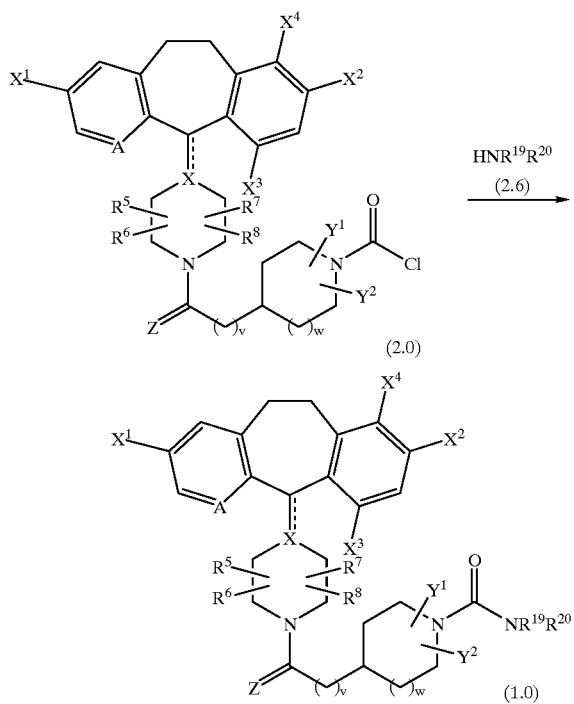

Referring to the Scheme I, compounds of formula (1.0) can be prepared by reacting the compounds of formula (2.0) with amine (NHR$^{19}$R$^{20}$) of formula (2.6) with an optional base and/or optional aprotic solvent such as THF, dioxane, acetonitrile, CH$_2$Cl$_2$ or DMF. In a first procedure, compound (2.0) is reacted with amine (2.6) neat, at temperatures ranging from about 0° to 80° C. In a second procedure, compound (2.0) is reacted with about equimolar amounts of amine (2.6) in the presence of a base such as sodium hydride and an aprotic solvent such as CH$_2$Cl$_2$ or THF. In a third procedure, compound (2.0) is reacted with amine (2.6) neat, using catalytic amounts of base, such as sodium hydride. In a fourth procedure, compound (2.0) is reacted with greater than two equivalents of amine (2.6) in an aprotic solvent at a temperature of about 75° C. Except as noted otherwise, temperatures can range from 0° to 100° C., or reflux of the reaction mixture and amounts of amine (2.6) can range from 1 to about 10 moles per mole of compound (2.0).

Scheme II

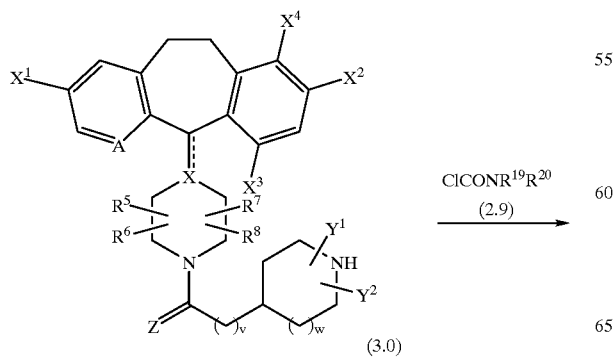

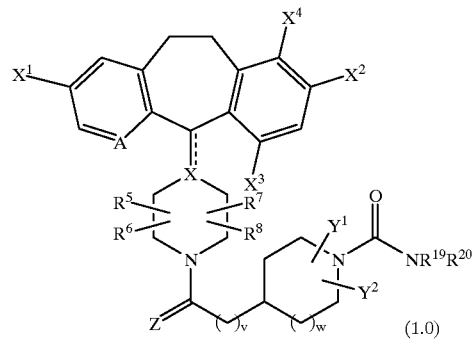

Referring to Scheme II, compounds of formula (1.0) can be prepared by reacting the compounds of formula (3.0) with carbonyl chloride of formula (2.9) with an optional base and/or optional aprotic solvent. In a first procedure, compound (3.0) is reacted with carbonyl chloride (2.9) neat, at temperatures ranging from about 0° C. to 80° C. In a second procedure, compound (3.0) is reacted with about equimolar amounts of carbonyl chloride (2.9) in the presence of a base such as sodium hydride and an aprotic solvent. In a third procedure, compound (3.0) is reacted with carbonyl chloride (2.9) neat, using catalytic amounts of base, such as sodium hydride. In a fourth procedure, compound (3.0) is reacted with greater than two equivalents of carbonyl chloride (2.9) in an aprotic solvent at a temperature of about 75° C. Except as noted otherwise, temperatures can range from 0° C. to 100° C., or reflux of the reaction mixture and amounts of carbonyl chloride (2.9) can range from 1 to about 10 moles per mole of compound (3.0).

Scheme III

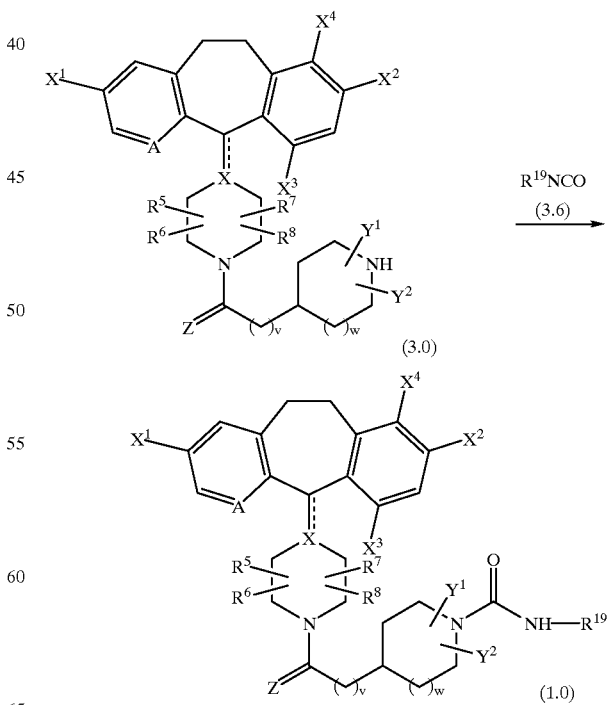

Referring to the Scheme III, compounds of formula (1.0) wherein $R^{20}$ is hydrogen (i.e. compound (1.0) is a monosubstituted urea) can be prepared by reacting the compounds of formula (3.0) with isocyanate $R^{19}$NCO of formula (3.6) with an optional base and/or optional aprotic solvent such as those described hereinbefore. In a first procedure, compound (3.0) is reacted with isocyanate (3.6) neat at temperatures ranging from about 0° to 80° C. In a second procedure, compound (3.0) is reacted with about equimolar amounts of isocyanate (3.6) in the presence of a base such as triethylamine and an aprotic solvent such as $CH_2Cl_2$ or THF. In a third procedure, compound (3.0) is reacted with about equimolar amounts of isocyanate (3.6) in the presence of a base such as sodium hydride and an aprotic solvent such as DMF or THF. In a fourth procedure, compound (3.0) is reacted with greater than two equivalents of isocyanate (3.6) in an aprotic solvent such as DMF at a temperature of about 75° C. In a fifth procedure, compound (3.0) is reacted with excess isocyanate (3.6) using catalytic amounts of a base such as sodium hydride and an aprotic solvent such as DMF or THF. Except as noted otherwise, temperatures can range from 0° to 100° C., or reflux of the reaction mixture and amounts of isocyanate (3.6) can range from 1 to about 10 moles per mole of compound (3.0).

Compounds of fomula (1.0) can be isolated from the reaction mixture using conventional procedures, such as, for example, extraction of the reaction mixture from water with organic solvents, evaporation of the organic solvents, followed by chromatography on silica gel or other suitable chromatographic media. Alternatively, compounds (1.0) can be dissolved in a water-miscible solvent, such as methanol, the methanol solution is added to water to precipitate the compound, and the precipitate is isolated by filtration or centrifugation.

(+)-Isomers of compounds of formula (5.0, 6.0 and 10.9) wherein X is CH can be prepared with high enantioselectivity by using a process comprising enzyme catalyzed transesterification. Preferably, a racemic compound of formula (5.0, 6.0 and 10.9), wherein X is C, the double bond is present and $X^3$ is not H, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of formula (5.0, 6.0 and 10.9), wherein X is C, the double bond is present and $R^3$ is not H, is first reduced to the corresponding racemic compound of formula (5.0, 6.0 and 10.9) wherein X is CH and then treated with the enzyme (Toyobo LIP-300) and acylating agent as described above to obtain the (+)-amide, which is hydrolyzed to obtain the optically enriched (+)-isomer.

Compounds of the present invention and preparative starting materials therof, are exemplified by the following examples, which should not be construed as limiting the scope of the disclosure.

EXAMPLE 1

(+)-4-[2-[4-[(3,10-Dibromo-8-chloro-6,11-dihydro-5H-benzo[5,6]cyclohepta[1,2-b]pyridin-11(R)-yl)-1-piperidinyl]-2-oxoethyl]-N-(2-methoxyphenyl)-1-piperidinecarboxamide

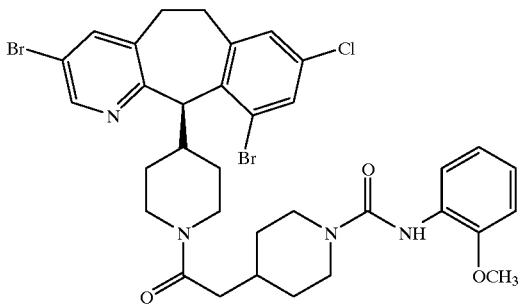

The title compound of Preparative Example 5 (90 mg, 0.15 mmol) was dissolved in 1.5 mL of anhydrous $CH_2Cl_2$ and 0.02 mL (0.2 mmol) 2-methoxyphenyl isocyanate was added. After 1 h the reaction was diluted with saturated $NaHCO_3$ solution (aqueous) and extracted with $CH_2Cl_2$. The combined organic extracts were washed with brine and water, dried ($MgSO_4$), filtered and the solvent evaporated. The residue was purified by preparative TLC using 5% ($NH_3$ saturated MeOH)/$CH_2Cl_2$ as eluent to afford 62 mg (52%) of the title compound as an off white solid (mp 135.2–137.0° C.).

EXAMPLE 2

(+)-4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-N-phenyl-1-piperidinecarboxamide

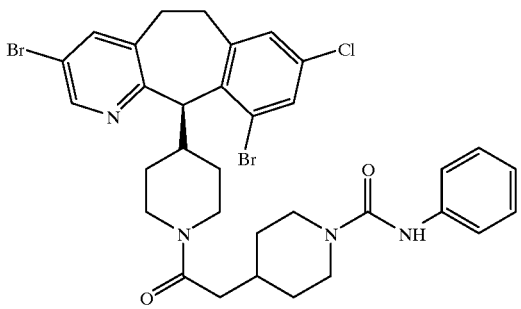

Following the procedure described in Example 1 using 90 mg (0.15 mmol) of the title compound of Preparative Example 5 and 0.02 mL (0.2 mmol) of phenyl isocyanate 58 mg (54%) of the title compound was obtained as an off white solid (mp 154.7–157.2° C.).

EXAMPLE 3

(+)-4-[2-[4-[(3,10-Dibromo-8-chloro-6,11-dihydro-5H-benzo[5,6]cyclohepta[1,2-b]pyridin-11(R)-yl)-1-piperidinyl]-2-oxoethyl]-N-methyl-1-piperidinecarboxamide

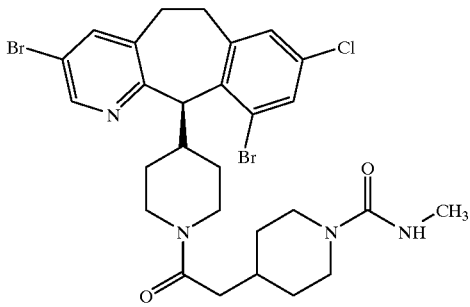

Following the procedure described in Example 1 using 90 mg (0.15 mmol) of the title compound of Preparative Example 5 and 0.01 mL (0.2 mmol) of methyl isocyanate and stirring the mixture overnight 53 mg (54%) of the title compound was obtained as a white solid (mp 108.5–110.3° C.).

EXAMPLE 4

(+)-Ethyl [[[4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinyl]carbonyl]amino]acetate

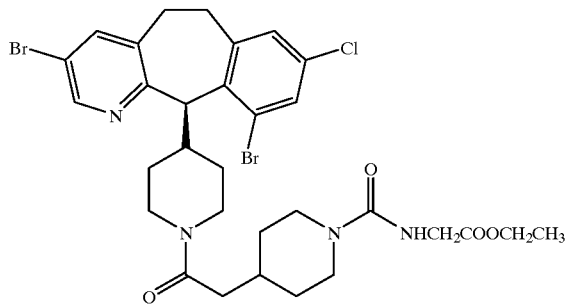

Following the procedure described in Example 1 using 90 mg (0.15 mmol) of the title compound of Preparative Example 5 and 0.02 mL (0.2 mmol) of ethyl isocyanatoacetate and stirring the mixture 2 h gave a material that was purified by flash chromatography (silica, 2%–4% (NH$_3$ saturated MeOH)/CH$_2$Cl$_2$ as eluent). The title compound was obtained as a white solid (45 mg, 40%, mp 126.4–128.2° C.).

EXAMPLE 5

(+)-Methyl alpha(S)-[[[4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinyl]carbonyl]amino]-beta-methylbutanoate

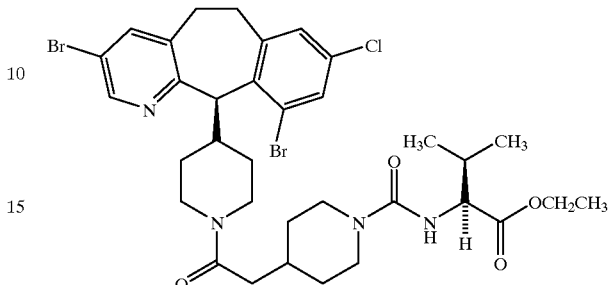

Following the procedure described in Example 1 using 90 mg (0.15 mmol) of the title compound of Preparative Example 5 and 49 mg (0.31 mmol) of (S)-(−)-2-isocyanato-3-methylbutyric acid methyl ester and stirring the mixture 3 h 102 mg (90%) of the title compound was obtained as a white solid without purification (mp 98.1–100.0° C.).

EXAMPLE 6

(+)-Ethyl 4-[[[4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinyl]carbonyl]amino]-1-piperidinecarboxylate

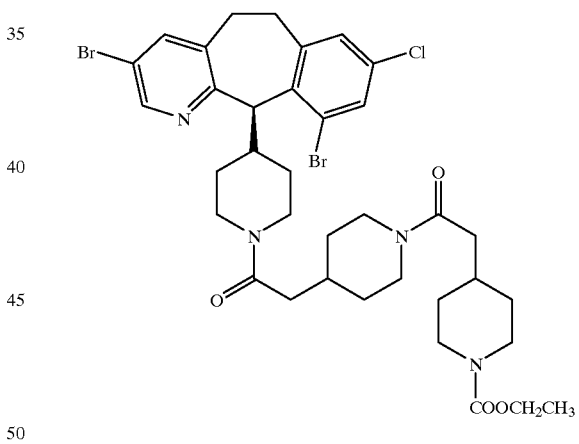

Ethyl 4-aminopiperidine carboxylate (1.00 ml, 5.83 mmol) was dissolved in anhydrous THF (5 ml) and the mixture was cooled to 0° C. A 1.93 M solution of phosgene in toluene (4.50 ml 8.69 mmol) was added followed by triethylamine (3.30 ml, 23.7 mmol). The resulting slurry was stirred at 0° C. 3 h then at room temperature overnight. The mixture was diluted with ether (20 mL), filtered and the filter cake washed with ether. The combined filtrate was evaporated to give a yellow oil 149 mg of which was dissolved in 1 mL anhydrous CH$_2$Cl$_2$ and added to a solution of the title compound of Preparative Example 5 in 2 mL of anhydrous CH$_2$Cl$_2$. After 3 h the mixture was diluted with saturated NaHCO$_3$ and extracted with CH$_2$Cl$_2$. The combined organic extracts were washed with brine, water, dried (MgSO$_4$), filtered and evaporated. The residue was purified by flash chromatography (silica, 2.5%–5% (NH$_3$ saturated MeOH)/

CH$_2$Cl$_2$ as eluent) to give the title compound (50 mg, 50%) as a white solid (mp 139.7–142.0° C.).

EXAMPLE 7

(+)-4-[2-[4-[(3,10-Dibromo -8-chloro-6,11-dihydro-5H-benzo[5,6]cyclohepta[1,2-b]pyridin-11(R)-yl)-1-piperidinyl]-2-oxoethyl]-N,N-bis(2-hydroxyethyl)-1-piperidinecarboxamide

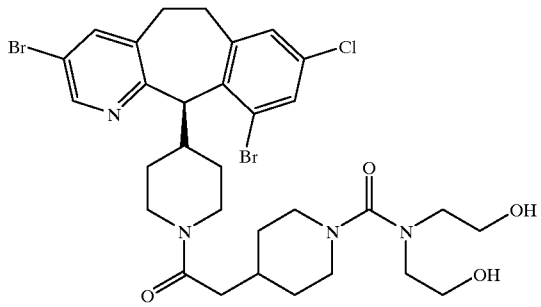

The title compound of Preparative Example 5 (200 mg, 0.34 mmol) was dissolved in anhydrous CH$_2$Cl$_2$ (2 mL) and 0.23 mL triethylamine (1.7 mmol). This solution was added to a 1.93 M solution of phosgene in toluene (0.88 mL, 1.7 mmol) at 0° C. and the resulting mixture was stirred at 0° C. for 1 hour. The mixture was evaporated and the residue stored under vacuum (10 mm Hg) overnight. This was dissolved in anhydrous CH$_2$Cl$_2$ (2 mL) and triethylamine (0.23 mL, 1.7 mmol) was added. To this was added a mixture of 0.04 mL diethanolamine hydrochloride (0.37 mmol) and triethylamine (0.1 mL, 0.74 mmol) in anhydrous CH$_2$Cl$_2$ (1 mL) and the mixture stirred 2 hours, diluted with 1 M NaOH and extracted with CH$_2$Cl$_2$. The combined extracts were washed with brine, dried (MgSO$_4$) and evaporated. The residue was purified by flash chromatography (2.5%, 5%, 10% (NH$_3$ saturated MeOH)/CH$_2$Cl$_2$ as eluent)) to give the product (79 mg, 32%) as a white solid (mp 105.3–107.4° C.).

EXAMPLE 8

(+)-Methyl 2(S)-[[[4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinyl]carbonyl]amino]-3-(1,1-dimethylethoxy)propanoate

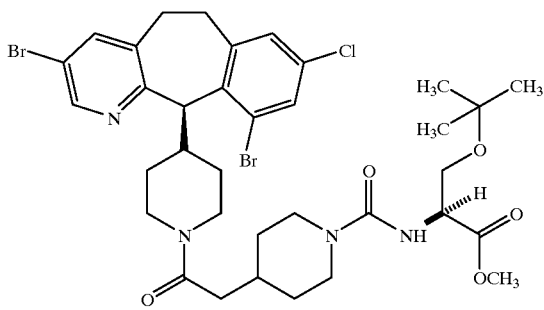

Following the procedure described in Example 1 using 450 mg (0.76 mmol) of the title compound of Preparative Example 5 and 369 mg (0.1.54 mmol) of methyl (S)-2-isocyanato-3-(1,1-dimethylethoxy)propanoate (J. S. Nowick et. al *J. Org. Chem.* 1992, 57, 7364) and stirring the mixture 3 h gave 459 mg (76%) of the title compound as a white solid after flash chromatography (silica, 5% (NH$_3$ saturated MeOH)/CH$_2$Cl$_2$ as eluent) mp 98.4–100.50° C.

EXAMPLE 9

(+)-Methyl 2(S)-[[[4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinyl]carbonyl]amino]-3-hydroxypropanoate

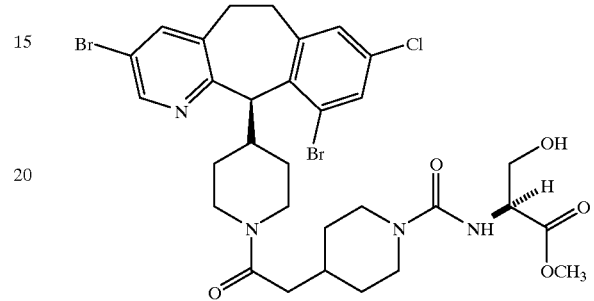

The title compound of Example 8 (330 mg, 0.41 mmol) was dissolved in anhydrous MeOH (2.5 mL) and 6 mL of 10% H$_2$SO$_4$/dioxane (v/v) was added. The mixture was stirred overnight then 0.2 mL conc. H$_2$SO$_4$ was added. After 4 h 1 M NaOH was added, water was added and the mixture extracted with CH$_2$Cl$_2$. The combined extracts were washed (brine), dried (MgSO$_4$), filtered and evaporated to give the title compound as a white solid (291.1 mg, 96%, mp 122.4–125° C.).

EXAMPLE 10

(+)-N-2[2-Amino-1(S)-(hydroxymethyl)-2-oxoethyl]-4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinecarboxamide

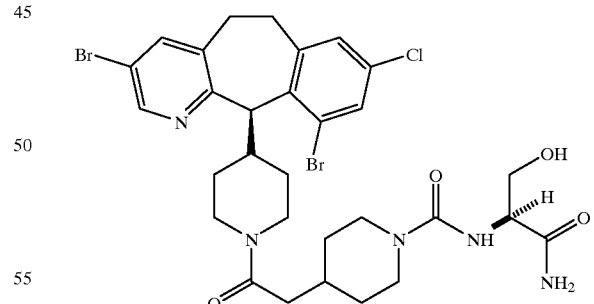

Similar to the procedure in Hogberg, T. et. al *J. Org. Chem.* 1987, 52, 2033, in a sealable vessel the title compound of Example 9 (99 mg, 0.13 mmol) was dissolved in 9 M NH$_4$OH/MeOH and 0.64 mg (0.013 mmol) NaCN was added. The sealed reaction vessel was heated at 50° C. (bath temperature) for 5 h, cooled to room temperature and stood overnight. The mixture was evaporated, the residue dissolved in CH$_2$Cl$_2$ and washed with H$_2$O. The aqueous wash was extracted with CH$_2$Cl$_2$, the combined extracts were dried (MgSO₄), filtered and evaporated to give the title compound as a white solid (30.4 mg, 32%, mp 150.5–153.30° C.)

EXAMPLE 11

(+)-4-[2-[4-[(3,10-Dibromo-8-chloro-6,11-dihydro-5H-benzo[5,6]cyclohepta[1,2-b]pyridin-11(R)-yl)-1-piperidinyl]-2-oxoethyl]-N-(2-hydroxyethyl)-1-piperidinecarboxamide

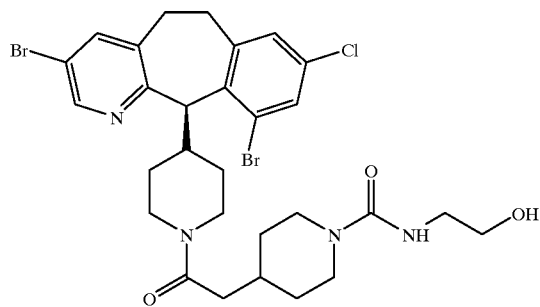

Following the procedure described in Example 7 using 200 mg (0.34 mmol) of the title compound of Preparative Example 5, 0.88 mL of 1.93 M phosgene in toluene (1.7 mmol), two 0.23 mL portions of triethylamine (1.7 mmol each) and 0.04 mL (0.66 mmol) of ethanolamine the title compound was obtained after precipitation from water as a brown solid (138.1 mg, 56%, mp 142.3–145.90° C.).

EXAMPLE 12

(+)-[[[4-[2-[4-[(3,10-Dibromo-8-chloro-6,11-dihydro-5H-benzo[5,6]cyclohepta[1,2-b]pyridin-11(R)-yl)-1-piperdinyl]-2-oxoethyl]-1-piperdinyl]carbonyl]amino]acetic acid

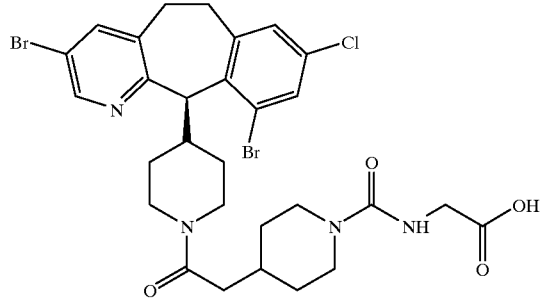

The title compound of Example 4 was dissolved in 6 M HCl and the mixture stirred 72 h. The reaction was diluted with H₂O and brine and extracted with CH₂Cl₂. The combined organic extracts were dried (MgSO₄), filtered and evaporated and the residue purified by flash chromatography (C₁₈ reverse phase silica (Aldrich), gradient elution, 1 L 50% MeOH/0.1% HOAc reservoir A, 1 L 90% MeOH/0.1% HOAc reservoir B) to give the title compound as a white solid (162.2 mg, 31%, mp 123.4–125.8° C.).

EXAMPLE 13

(+)-N-(2-Amino-2-oxoethyl)-4-[2-[4-[(3,10-dibromo-8-chloro-6,11-dihydro-5H-benzo[5,6]cyclohepta[1,2-b]pyridin-11(R)-yl)-1-piperidinyl]-2-oxoethyl]-1-piperidinecarboxamide

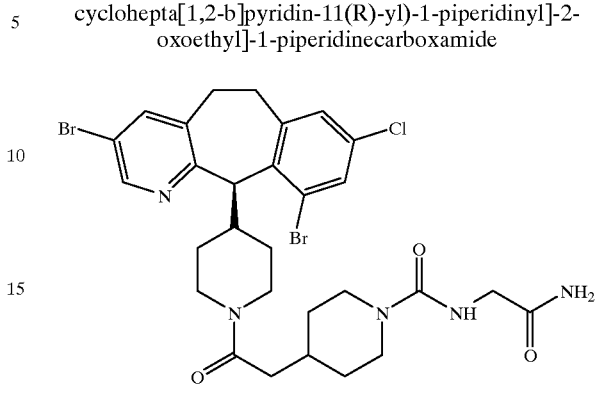

The title compound of Example 12 (60 mg, 0.086 mmol) was dissolved in DMF and NH₄Cl (7 mg, 0.13 mmol), N-methylmorpholine (0.015 mL, 0.13 mmol), 1-(3-dimethylaminopropyl)-3-ethylcarbodiimide hydrochloride (25 mg, 0.13 mmol) and 1-hydroxybenzotriazole hydrate (17 mg, 0.13 mmol) were added. After 3.5 h an additional 21 mg of NH₄Cl (0.39 mmol) was added and the mixture stirred overnight. Water was added to give the title compound as a white solid (33.4 mg, 55%, mp 144.8–149.80° C.).

EXAMPLE 14

4-[2-[4-(3-Bromo-8-chloro-6,11-dihydro-5H-benzo[5,6]-cyclohepta[1,2-b]pyridin-11-yl)-1-piperazinyl]-2-oxoethyl]-N-methyl-1-piperidinecarboxamide

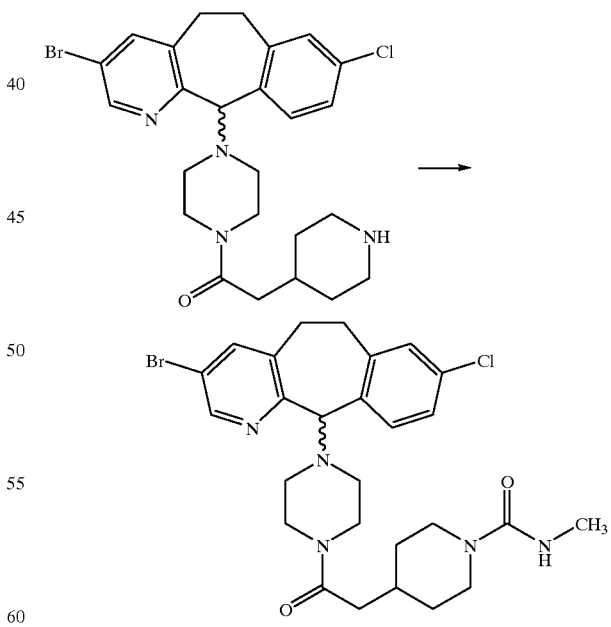

1-(3-Bromo-8-chloro-6,11-dihydro-5H-benzo[5,6]cyclohepta[1,2-b]pyridin-11-yl)-4-[(4-piperidinyl)acetyl]piperazine (Preparative Example 10) (500 mg, 0.9 mmoles) was dissolved in anhydrous dichloromethane (5 ml) and methyl isocyanate (220.3 mg, 3.6 mmoles) was added. The mixture was stirred under argon at 25° C. for 47 h. Additional methyl isocyanate (110.15 mg, 1.8 mmoles) was added and the reaction was stirred for a total of 144 h. The solution was heated at 74° C. for 5 h and the stirred at 25° C. for an additional 24 h. The solution was chromatographed on silica gel using 2% (10% conc. NH$_4$OH in methanol) dichloromethane as the eluant to give 438.9 mg of the title compound (Yield: 79%).

EXAMPLE 15

4-[2-[4-(3-Bromo-8-chloro-6,11-dihydro-5H-benzo[5,6]cyclohepta[1,2-b]pyridin-11-yl)-1-piperazinyl]-2-oxoethyl]-N-propyl-1-piperidinecarboxamide

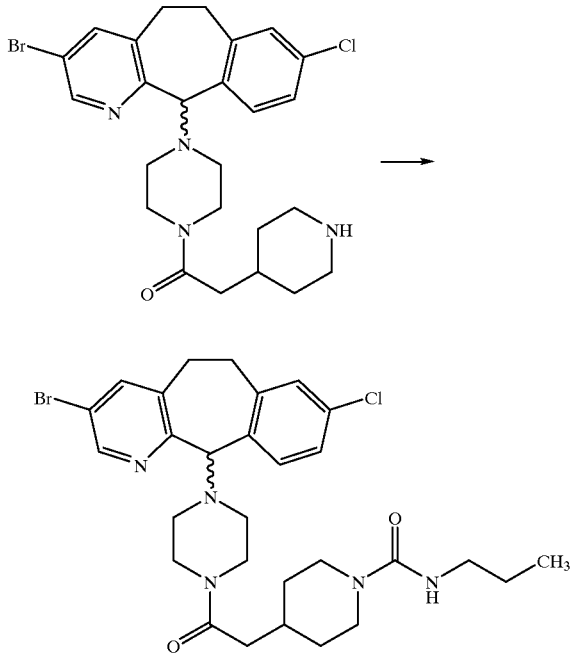

1-(3-Bromo-8-chloro-6,11-dihydro-5H-benzo[5,6]cyclohepta[1,2-b]pyridin-11-yl)-4-[(4-piperidinyl)acetyl]piperazine (Preparative Example 10) (490 mg, 0.8 mmoles) was dissolved in anhydrous dichloromethane (5 ml) and n-propyl isocyanate (322.1 mg, 3.2 mmoles) was added. The mixture was stirred under argon at 25° C. for 44 h. The solution was chromatographed on silica gel using 2% (10% concentrated NH$_4$OH in methanol)dichloromethane as the eluant to give 544.8 mg of the title compound (Yield: 95%).

EXAMPLE 16

4-[2-[4-(3-Bromo-8-chloro-6,11-dihydro-5H-benzo[5,6]cyclohepta[1,2-b]pyridin-11-yl)-1-piperazinyl]-2-oxoethyl]-N-(1,1-dimethylethyl)-1-piperidinecarboxamide

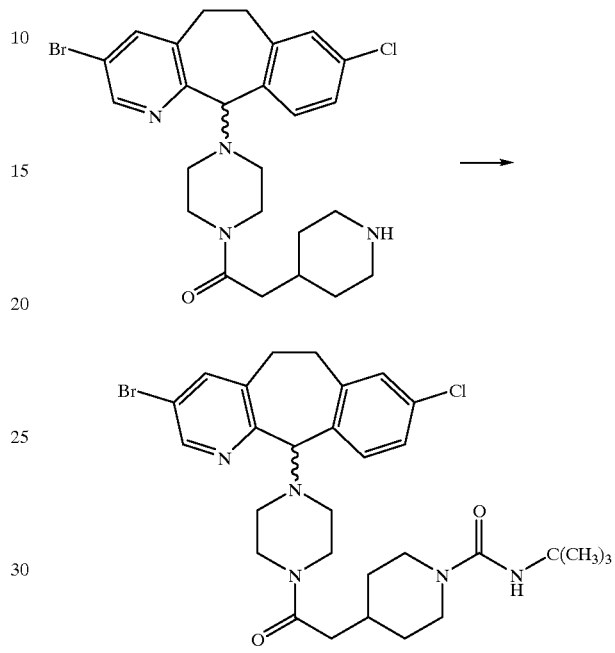

1-(3-Bromo-8-chloro-6,11-dihydro-5H-benzo[5,6]cyclohepta[1,2-b]pyridin-11-yl)-4-[(4-piperidinyl)acetyl]piperazine (Preparative Example 10) (500 mg, 0.8 mmoles) was dissolved in anhydrous dichloromethane (5 ml) and tert-butyl isocyanate (383.8 mg, 3.2 mmoles) was added. The mixture was stirred under argon at 25° C. for 47 h. Additional tert-butyl isocyanate (191.4 mg, 1.6 mmoles) was added and the reaction was stirred for a total of 144 h. The solution was heated at 74° C. for 5 h and the stirred at 25° C. for an additional 24 h. The solution was chromatographed on silica gel using 2% (10% conc. NH$_4$OH in methanol) dichloromethane as the eluant to give 421.8 mg of the title compound (Yield: 71%).

Preparation of Starting Materials

Starting materials useful in preparing the compounds of the present invention are exemplified by the following preparative examples, which should not be construed to limit the scope of the disclosure. The tricyclic compounds used as starting materials, such as compound (11.0), inorganic and organic bases, and alcohols can be prepared using known methods in the art, such as taught in See J. K. Wong et al., Bioorganic & Medicinal Chemistry Letters, Vol. 3, No. 6, pp. 1073–1078, (1993); U.S. Pat. Nos. 5,089,496; 5,151,423; 4,454,143; 4,355,036; PCT/US94/11390 (WO95/10514); PCT/US94/11391 (WO 95/10515); PCT/

US94/11392 (WO95/10516); Stanley R. Sandier and Wolf Karo, Organic Functional Group Preparations, 2nd Edition, Academic Press, Inc., San Diego, Calif., Vol. 1–3, (1983), and in J. March, Advanced Organic Chemistry, Reactions & Mechanisms, and Structure, 3rd Edition, John Wiley & Sons, New York, 1346 pp. (1985). Alternative mechanistic pathways and analogous structures within the scope of the invention may be apparent to those skilled in the art.

Starting materials used to prepare the compounds of the present invention are depicted in Scheme IV:

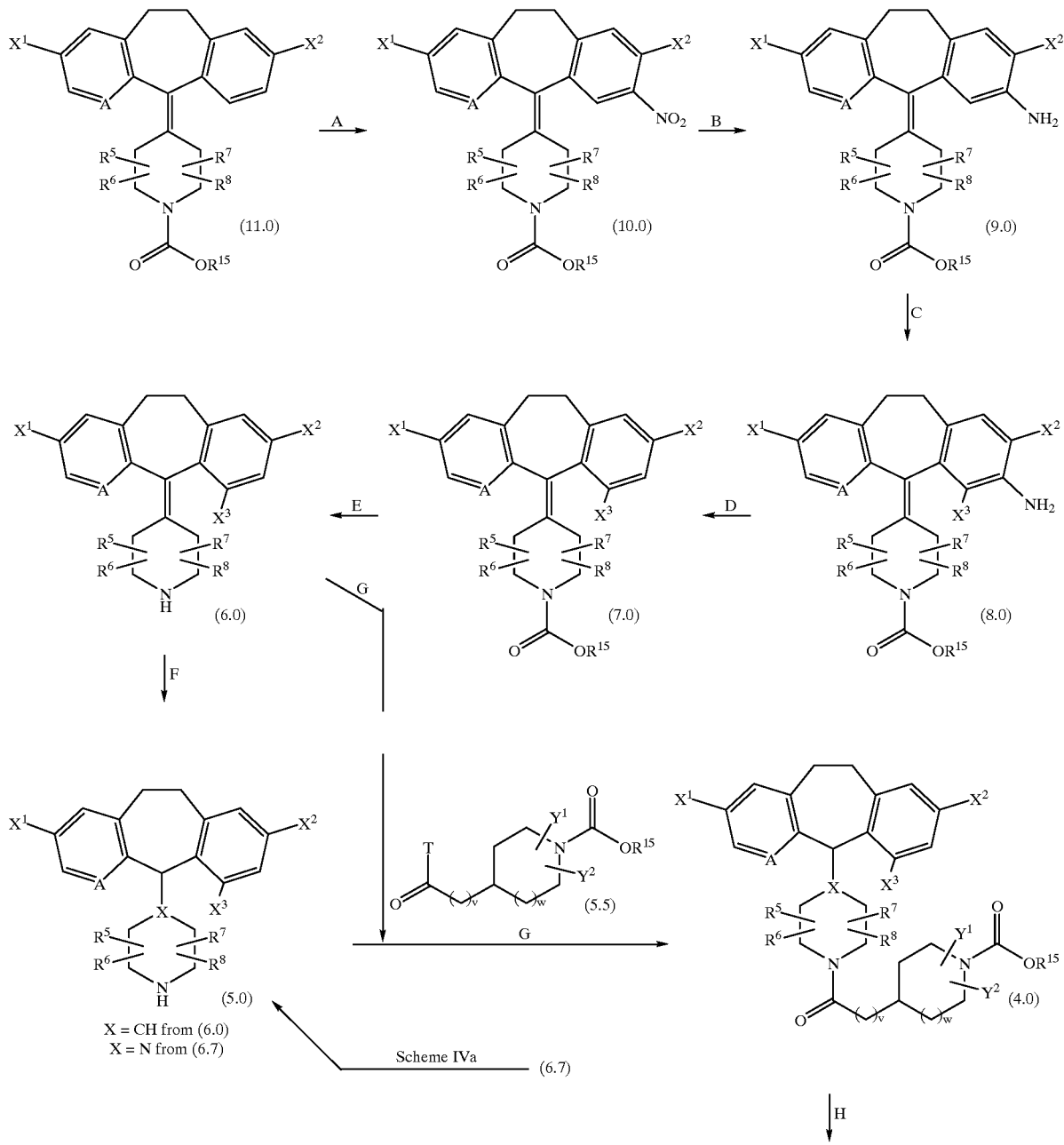

-continued

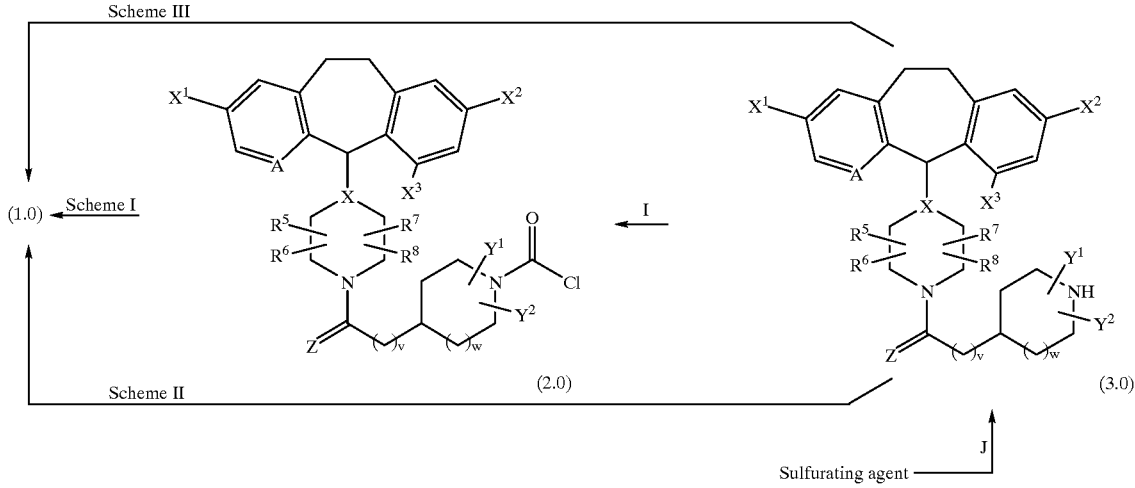

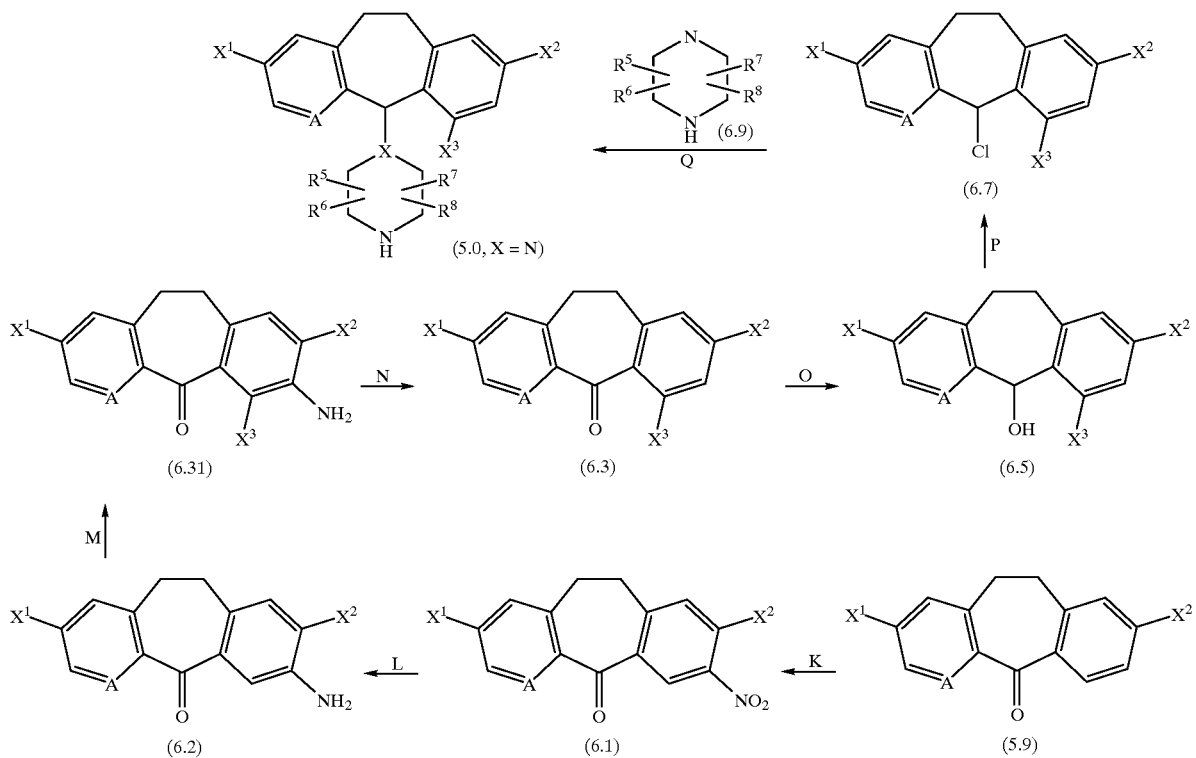

wherein for Schemes IV and IVa,
X, X¹, X², X³, Y¹, Y², Z, R⁵, R⁶, R⁷ and R⁸, R¹⁹, R²⁰, v, w, the lines are as defined hereinbefore; and R¹⁵ can represent any of the values for R¹⁰ as defined hereinbefore; and T is OH, —OCOR¹⁰, halo such as chloro or —OR¹⁰.

In Step A (Scheme IV), compounds of formula (10.0) can be prepared by reacting the compounds of formula (11.0) with a nitrating agent and/or optional protic or aprotic solvent such as those described hereinbefore. In a first procedure, compound (11.0) is reacted with about an equimolar amount of a nitrate salt, such as potassium nitrate, and acid, such as sulfuric acid at temperatures ranging from about −20° to +50 C. In a second procedure, compound (11.0) is reacted with about an equimolar amount of nitric acid and acid, such as sulfuric acid at temperatures ranging from about −20° to +50° C. In a third procedure, compound (11.0) is treated with a mixture comprised of about two equivalents of trifluoromethanesulfonic acid and about one equivalent nitric acid in a solvent such as trifluoromethanesulfonic acid. In a fourth procedure, compound (11.0) is treated with a mixture comprised of about one equivalent of fuming nitric acid and about ten equivalents of trifluoromethanesulfonic anhydride in a solvent such as nitromethane. In a fifth procedure, compound (11.0) is treated with a nitronium salt, such as nitronium tetrafluoroborate, in a solvent, such as sulfolane. In a sixth procedure, compound (11.0) is reacted with fuming nitric acid at temperatures ranging from about −20° to +50° C.

In Step B(Scheme IV), compounds of formula (9.0) can be prepared by reacting compounds of the formula (10.0) with a reducing agent. In a first procedure, compound (10.0) can be reacted with about ten equivalents of a metal, such as iron, in a solvent, such as ethanol, in the presence of a salt, such as calcium chloride, at temperatures ranging from about 0° to +80° C. In a second procedure, compound (10.0) can be reacted with about ten equivalents of a metal, such as zinc, in a solvent, such as ethanol, in the presence of an acid, such as acetic acid at temperatures ranging from about 0° to +80° C. In a third procedure, compound (10.0) can be reacted with about five equivalents of stannous chloride hydrate in a solvent, such as ethyl acetate. In a fourth procedure, compound (10.0) can be reacted with about ten equivalents of a metal, such as tin, in a solvent, such as ethanol, in the presence of an acid, such as hydrochloric acid.

In Step C(Scheme IV), compounds of formula (8.0) can be prepared by reacting compounds of the formula (9.0) with a halogenating agent. In a first procedure, compound (9.0) can be reacted with an excess of an elemental halogen, such as bromine, in a suitable solvent, such as acetic acid at temperatures ranging from about 0° to +80° C. In a second procedure, compound (9.0) can be reacted with an excess of a mineral acid, such as hydrogen bromide, in a suitable solvent, such as dimethyl sulfoxide at temperatures ranging from about 20° C. to about 135° C. In a third procedure, compound (9.0) can be reacted with a salt, such as pyridinium bromide perbromide, in a solvent, such as THF, at temperatures from about 0° to +40° C. In a fourth procedure, compound (9.0) can be reacted with a halogen, such as chlorine, in the presence of a Lewis acid, such as iron(III) chloride, in a suitable solvent, such as dichloromethane.

In Step D(Scheme IV), compounds of formula (7.0) can be prepared by reacting compounds of the formula (8.0) with an oxidizing agent followed by a reducing agent, or by reacting compounds of the formula (8.0) with an oxidizing agent in the presence of a hydrogen atom source. In a first procedure, compound (8.0) can be reacted with a diazotizing agent, such as t-butyl nitrite, in a solvent and hydrogen atom source, such as DMF at temperatures from about 0° to +100° C. In a second procedure, compound (8.0) can be reacted with a diazotizing agent, such as sodium nitrite, and an acid, such as hydrochloric acid, and a reducing agent, such as hypophosphorous acid at temperatures from about −15° to +50° C. In a third procedure, compound (8.0) can be reacted with a diazotizing agent, such as sodium nitrite, and an acid, such as aqueous sulfuric acid, followed by treatment with a metal, such as copper. In a fourth procedure, compound (8.0) can be reacted with a diazotizing agent, such as sodium nitrite, and an acid, such as fluoboric acid, followed by treatment with a reducing agent, such as sodium borohydride.

In Step E(Scheme IV), compounds of formula (6.0) can be prepared by reacting compounds of the formula (7.0) under hydrolysis conditions. In a first procedure, compound (7.0) can be reacted with an acid, such as hydrochloric acid, at temperatures from about 20° to +90° C. In a second procedure, compound (7.0) can be reacted with a base, such as aqueous sodium hydroxide, in a suitable solvent, such as ethanol, at temperatures from about 20° to +90° C. In a third procedure, compound (7.0) can be reacted with a nucleophile, such as hydrazine hydrate, in a solvent, such as ethanol, with an optional base, such as sodium hydroxide, at temperatures from about 20° to +90° C. In a fourth procedure, compound (7.0) can be reacted with a silyl chloride, such as trimethylsilyl chloride, in a solvent, such as THF or $CH_2Cl_2$ at temperatures ranging from about 0° C. to reflux. In a fifth procedure, compound (7.0) can be reacted with an acid, such as trifluoroacetic acid, in an aprotic solvent, such as $CH_2Cl_2$.

In Step F(Scheme IV), compounds of formula (5.0) wherein X=CH can be prepared by reacting compounds of the formula (6.0) under reducing conditions. Compound (6.0) can be reacted with an alkyl-metal hydride, such as diisobutyl aluminum hydride, in a solvent, such as toluene, at temperatures from about 0° to +90° C.

In Step G(Scheme IV), compounds of formula (4.0) can be prepared by reacting compounds of the formula (5.0) with a carboxylic acid under dehydrating conditions. In a first example, compound (5.0) or (6.0) can be reacted with carboxylic acid (5.5 wherein T=—OH) in the presence of a carbodiimide, such as DEC, with an optional base, such as 1-methylmorpholine, with an optional catalyst, such as HOBT, in a solvent such as DMF. In a second example, compound (5.0) or (6.0) can be reacted with an carboxylic anhydride in a protic or aprotic solvent such as THF. In a third example, compound (5.0) or (6.0) can be reacted with a carboxylic acid chloride (5.5 wherein T=Cl) in an aprotic solvent such as THF or $CH_2Cl_2$. In a fourth example, compound (5.0) or (6.0) can be reacted with an carboxylic acid ester (5.5 wherein T=—$OR^{10}$), such as a pentafluorophenyl ester, in an aprotic solvent such as THF or $CH_2Cl_2$.

In Step H(Scheme IV), compounds of formula (3.0) can be prepared by reacting compounds of the formula (4.0) under hydrolysis conditions. In a first procedure, compound (4.0) can be reacted with an acid, such as hydrochloric acid, at temperatures from about 20° to +90° C. In a second procedure, compound (4.0) can be reacted with a base, such as aqueous sodium hydroxide, in a suitable solvent, such as ethanol, at temperatures from about 2° to +90° C. In a third procedure, compound (4.0) can be reacted with a nucleophile, such as hydrazine hydrate, in a solvent, such as ethanol, with an optional base, such as sodium hydroxide, at temperatures from about 20° to +90° C. In a fourth procedure, compound (4.0) can be reacted with a silyl chloride, such as trimethylsilyl chloride, in a solvent, such as THF or $CH_2Cl_2$. In a fifth procedure, compound (4.0) can be reacted with an acid, such as trifluoroacetic acid, in an aprotic solvent, such as $CH_2Cl_2$.

In Step I (Scheme IV), compounds of formula (2.0) can be prepared by reacting compounds of the formula (3.0) and (3.1) with an excess amount of phosgene or a compound capable of releasing phosgene, in the presence of an optional base, such as $Et_3N$, either neat, or in an optional aprotic solvent.

In Step J, the sulfur-containing compounds of formula (3.0) wherein Z=S, can be prepared by the amide (3.0) can be reacted with a sulfurating agent such as Lawesson's Reagent in a suitable aprotic solvent such as toluene at about 100° C. to give the thioamide (3.1). Alternative sulfurating reagents include bis-(1,5-cyclooctanediarylboryl)sulfide in hexane at −78° C.; or phosphorous pentasulfide ($P_2S_5$, also of the formula $P_4S_{10}$) in toluene at reflux temperatures, or in THF using ultrasound at 40° C.; or bis-(9-Borabicyclo[3.3.1]nonane)sulfide (($9$-$BBN)_2S$) in heptane at reflux temperatures.

In Step K(Scheme IVa), compounds of formula (6.1) can be prepared by reacting the compound of formula (5.9) with a nitrating agent and/or optional protic or aprotic solvent according to the procedures described in Step A (Scheme IV).

In Step L (Scheme IVa), compounds of formula (6.2) can be prepared by reacting the compound of formula (6.1) with a reducing agent according to the procedures described in Step B (Scheme IV).

In Step M (Scheme IVa), compounds of formula (6.31) can be prepared by reacting the compound of formula (6.2) with a halogenating agent according to the procedures described in Step C (Scheme IV).

In Step N (Scheme IVa), compounds of formula (6.3) can be prepared by reacting the compound of formula (6.31) with an oxidizing agent followed by a reducing agent, or by reacting compounds of the formula (6.31) with an oxidizing agent in the presence of a hydrogen atom source according to the procedures described in Step D (Scheme IV).

In Step O(Scheme IVa), compounds of formula (6.5) can be prepared by reacting compounds of formula (6.3) with sodium borohydride ($NaBH_4$) in a solvent such as ethanol/toluene under reflux conditions for 10 minutes or at 25° C. for two hours or more.

In Step P (Scheme IVa), compounds of formula (6.7) can be prepared by reacting compounds of formula (6.5) with $SOCl_2$ in a solvent such as $CH_2Cl_2$ at a temperature of about 25° C. for about 4 hours or more.

In Step Q (Scheme IVa), compounds of formula (5.0) wherein X=N, can be prepared by reacting compounds (6.7) with an excess amount of the piperazine compound of formula (6.9) in a solvent such as THF at 25° C. or reflux for one hour or more.

Additional starting materials which can be used to prepare the compounds of the present invention are depicted in Scheme V.

Scheme V

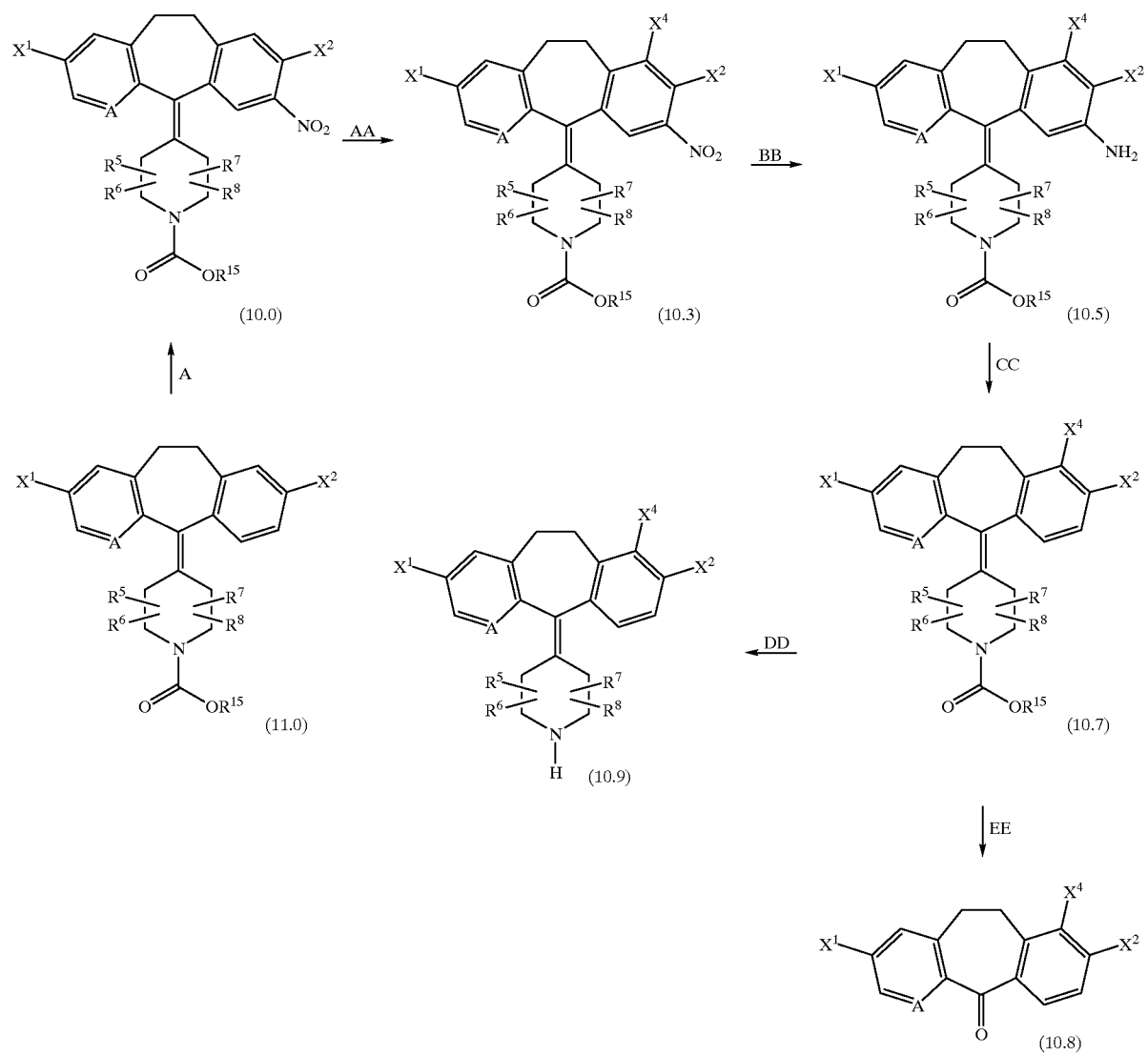

In Step A (Scheme V), compounds of fomula (10.0) can be prepared from compound of formula (11.0) using the procedures described in Scheme IV, Step A.

In Step AA(Scheme V), compounds of formula (10.3) can be prepared by reacting compound of formula (10.0) with 1,3-dibromo-5,5-dimethylhydantoin in an acid, such as trifluoromethane sulfonic acid or sulfuric acid for about 24 h or more at 25° C.

In Step BB (Scheme V), compounds of the formula (10.5) can be prepared by treating the compounds of formula (10.3) with a reducing agent, using the procedures taught in Scheme IV, Step B.

In Step CC (Scheme V), compounds of formula (10.7) can be prepared by reacting compounds of formula (10.5) with sodium nitrite ($NaNO_2$) in concentrated aqueous HCl at temperatures ranging from about −10° C. to 0° C. for about 2 h or more, then treating the reaction mixture with phosphorous acid ($H_3PO_2$) at 0° C. for 4 h or more.

In Step DD(Scheme V), compounds of formula (10.9) can be prepared by reacting compounds of formula (10.7) with concentrated aqueous HCl at about 85° C. for about 18 h or more. Compound (10.9) can be reacted using the same procedures described in Scheme IV for treating compound (5.0) and (6.0) and subsequent intermediates therefrom, in order to obtain the desired compounds of formula (1.0).

In Step EE (Scheme V), compounds of formula (10.8) can be prepared by reacting compound of formula (10.7) with $NaIO_4$ and $RuO_2$ in acetonitrile and water for about 18 to 24 h or more at 25° C. Compound (10.8) can be reacted using the same procedures described in Scheme IVa for treating compound (6.3) and subsequent intermediates therefrom, such as compound (5.0) or (6.0), in order to obtain the desired compounds of formula (1.0).

Referring to the Schemes IV, IVa and V, except as noted otherwise, temperatures can range from 0° to 100° C., or reflux of the reaction mixture and amounts of the reagents (e.g. compound 5.5) can range from 1 to about 10 moles per mole of reactant (e.g. compound 5.0 or 6.0).

The following preparative examples are intended to exemplify selected starting materials for preparing compounds of the present invention.

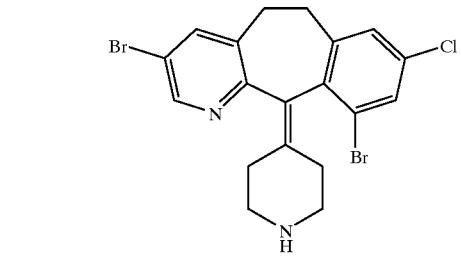

Preparative Example 1

Step A

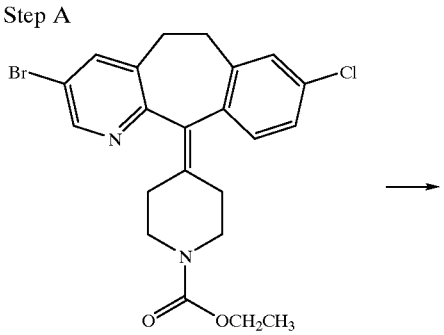

-continued

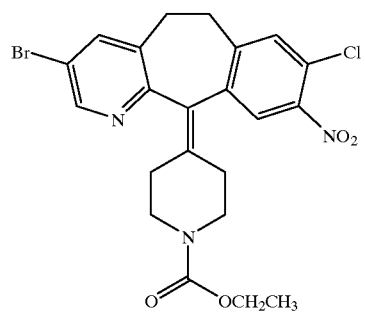

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester (as taught in Preparative Example 47 of PCT/US 94/11392) and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product.

Step B

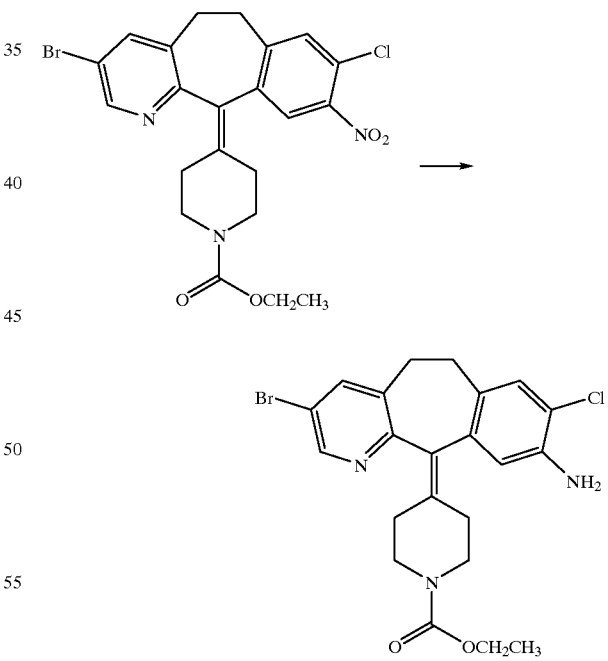

Combine 6.69 g (13.1 mmol) of the product of Step A and 100 ml of 85% EtOH/water, then add 0.66 g (5.9 mmol) of $CaCl_2$ and 6.56 g (117.9 mmol) of Fe and heat the mixture at reflux overnight. Filter the hot reaction mixture through Celite® and rinse the filter cake with hot EtOH. Concentrate the filtrate in vacuo to give 7.72 g of the product.

Step C

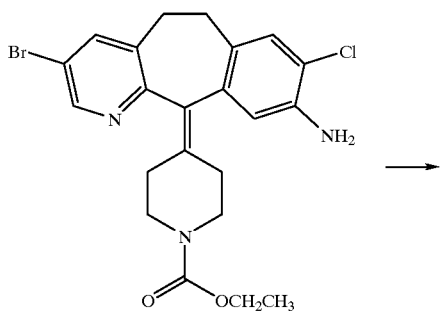

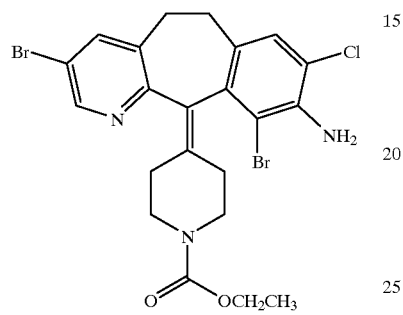

Combine 7.70 g of the product of Step B and 35 ml of HOAc, then add 45 ml of a solution of $Br_2$ in HOAc and stir the mixture at room temperature overnight. Add 300 ml of 1 N NaOH (aqueous), then 75 ml of 50% NaOH (aqueous) and extract with EtOAc. Dry the extract over $MgSO_4$ and concentrate in vacuo to a residue. Chromatograph the residue (silica gel, 20%–30% EtOAc/hexane) to give 3.47 g of the product (along with another 1.28 g of partially purified product).

Step D

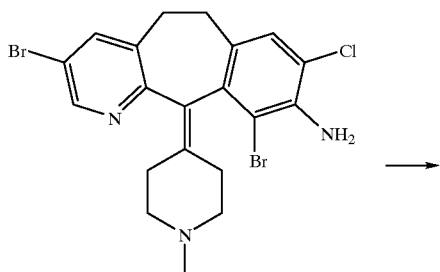

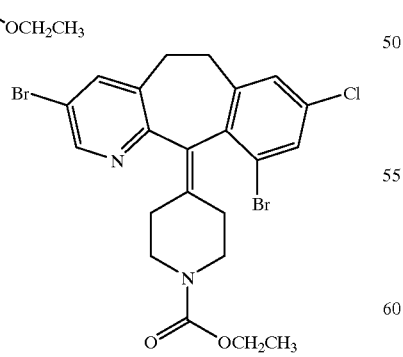

Combine 0.557 g (5.4 mmol) of t-butylnitrite and 3 ml of DMF, and heat the mixture at to 60°–70° C. Slowly add (dropwise) a mixture of 2.00 g (3.6 mmol) of the product of Step C and 4 ml of DMF, then cool the mixture to room temperature. Add another 0.64 ml of t-butylnitrite at 40° C. and reheat the mixture to 60°–70° C. for 0.5 hrs. Cool to room temperature and pour the mixture into 150 ml of water. Extract with $CH_2Cl_2$, dry the extract over $MgSO_4$ and concentrate in vacuo to a residue. Chromatograph the residue (silica gel, 10%–20% EtOAc/hexane) to give 0.74 g of the product.

Step E

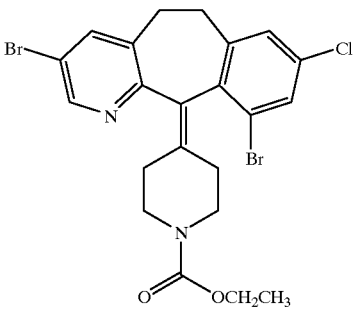

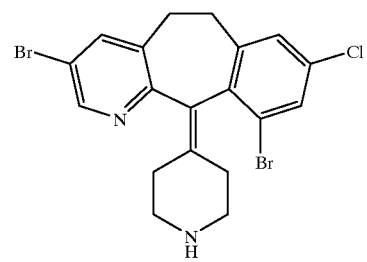

Combine 0.70 g (1.4 mmol) of the product of Step D and 8 ml of concentrated HCl (aqueous) and heat the mixture at reflux overnight. Add 30 mL of 1 N NaOH (aqueous), then 5 ml of 50% NaOH (aqueous) and extract with $CH_2Cl_2$. Dry the extract over $MgSO_4$ and concentrate in vacuo to give 0.59 g of the title compound.

Preparative Example 2

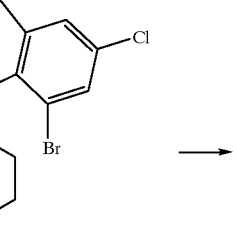

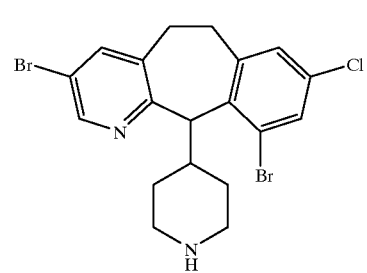

Prepare a solution of 8.1 g of the title compound from Preparative Example 7 in toluene and add 17.3 ml of a 1M solution of DIBAL (diisobutyl aluminum hydride) in toluene. Heat the mixture at reflux and slowly add (dropwise) another 21 ml of 1 M DIBAL/toluene solution over a period of 40 min. Cool the reaction mixture to about 0° C. and add 700 ml of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Preparative Example 3

Separation of Enantiomers

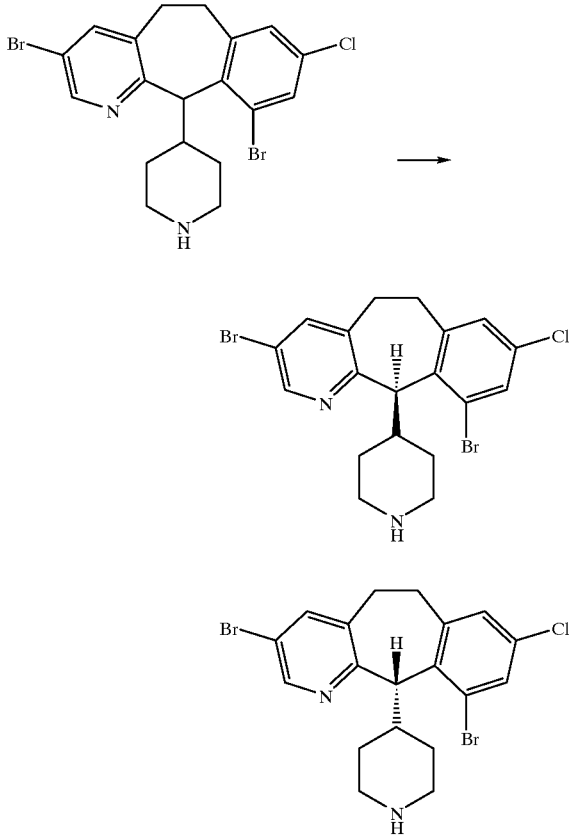

The racemic title compound of Preparative Example 1 is separated by preparative chiral chromatography (Chiralpack AD, 5 cm×50 cm column, using 20% iPrOH/hexane+0.2% diethylamine), to give the (+)-isomer and the (−)-isomer of the title compound. Altenatively, the enantiomers can also be separated by crystallization with an amino acid such as N-acetylphenylalanine.

Preparative Example 4

(+)-1,1-Dimethylethyl 4-[2-[4-(3,10-dibromo-8-chloro-6,11-dihydro-5H-benzo[5,6]cyclohepta[1,2-b]pyridin-11(R)-yl)-1-piperidinyl]-2-oxoethyl]-1-piperdinecarboxylate

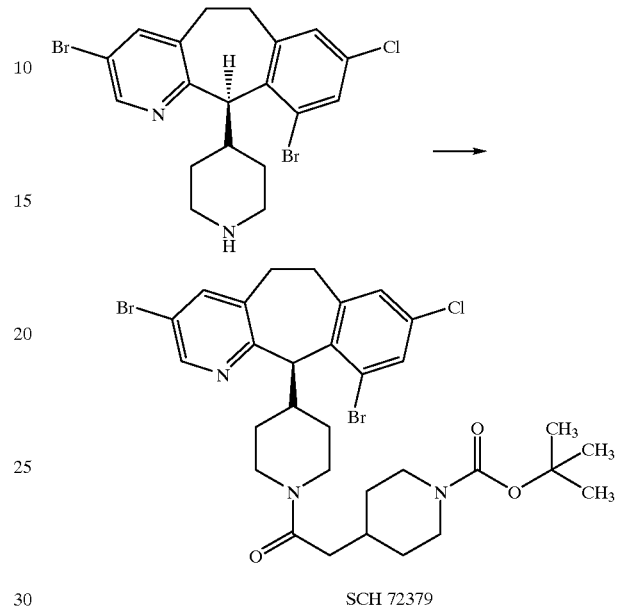

SCH 72379

Combine 2.56 g (5.44 mmol) of the (+)-isomer of Preparative Example 3 with 1.71 g (7.03 mmol) of N-BOC-4-piperidylacetic acid, 1.01 g (7.47 mmol) 1-hydroxybenzotriazole hydrate and 1.40 ml (12.7 mmol) N-methylmorpholine in 15 ml of anhydrous DMF and add 1.29 g (6.73 mmol) of 1-(3-dimethylaminopropyl)-3-ethylcarbodiimide hydrochloride and stir at room temperature for 5 h. The mixture was diluted with 15 ml water and 15 ml saturated $NaHCO_3$ solution (aqueous) and extracted with ethyl acetate. The organic extracts were washed with saturated $NaHCO_3$ solution, brine and dried ($MgSO_4$) to give the product.

Preparative Example 5

(+)-4-(8-Chloro-3,10-dibromo-6,11-dihydro-5H-benzo[5,6]cyclohepta-[1,2-b]pyridin-11-yl)-1-(4-piperidinylacetyl)piperidine

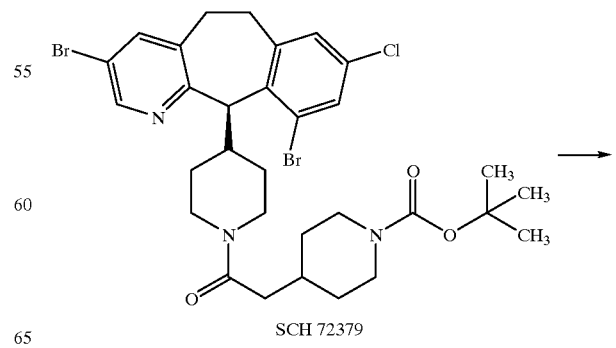

SCH 72379

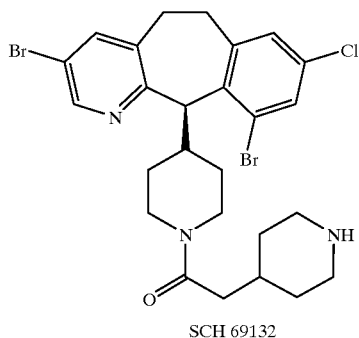

SCH 69132

The title compound of Preparative Example 4 (4.10 g, 5.44 mmol) was suspended in 10% H₂SO₄/dioxane (v/v) and small potions of methanol were added till a clear solution resulted. After 2 h at room temperature 10% NaOH solution (aqueous) was added untill the mixture became cloudy and this was diluted with ethyl acetate. The aqueous layer was adjusted to pH 8–9 with 10% NaOH solution, the layers were separated and the aqueous mixture extracted with ethyl acetate. The combined organic mixture was washed with brine, dried (MgSO₄) and evaporated to give the product (2.77 g, 85%).

Preparative Example 6

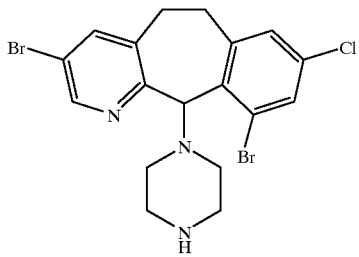

[racemic as well as (+)- and (−)-enantiomer]

Step A

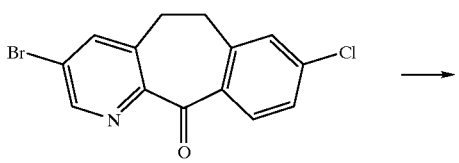

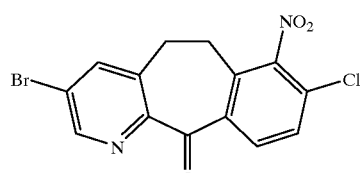

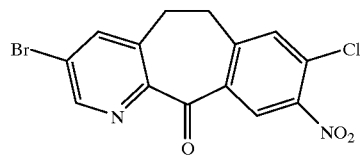

Combine 40.0 g (0.124 mole) of the starting ketone (as taught in Preparative Example 20 of PCT/US 94/11392) and 200 ml of H₂SO₄ and cool to 0° C. Slowly add 13.78 g (0.136 mole) of KNO₃ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds. MH⁺ (9-nitro)=367.

Step B

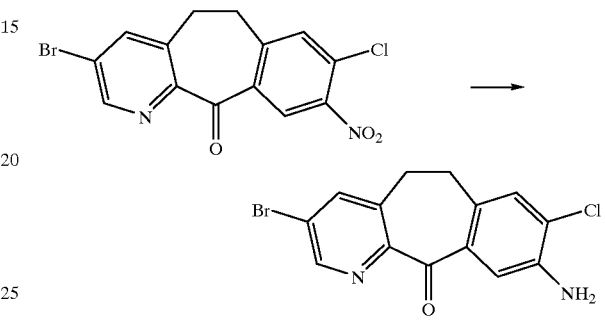

React 28 g (76.2 mmol) of the 9-nitro product of Step A, 400 ml of 85% EtOH/water, 3.8 g (34.3 mmol) of CaCl₂ and 38.28 g (0.685 mole) of Fe at 50° C. Heat the mixture at reflux overnight, filter through Celite® and wash the filter cake with 2×200 ml of hot EtOH. Combine the filtrate and washes, and concentrate in vacuo to a residue. Extract the residue with 600 ml of CH₂Cl₂, wash with 300 ml of water and dry over MgSO₄. Filter and concentrate in vacuo to a residue, then chromatograph (silica gel, 30% EtOAc/CH₂Cl₂) to give 24 g of the product.

Step C

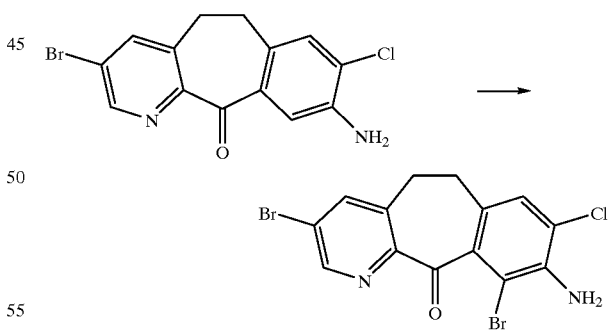

Combine 13 g (38.5 mmol) of the product of Step B, 140 ml of HOAc and slowly add a solution of 2.95 ml (57.8 mmol) of Br₂ in 10 ml of HOAc over a period of 20 min. Stir the reaction mixture at room temperature, then concentrate in vacuo to a residue. Add CH₂Cl₂ and water, then adjust to pH=8–9 with 50% NaOH (aqueous). Wash the organic phase with water, then brine and dry over Na₂SO₄. Concentrate in vacuo to give 11.3 g of the product.

Step D

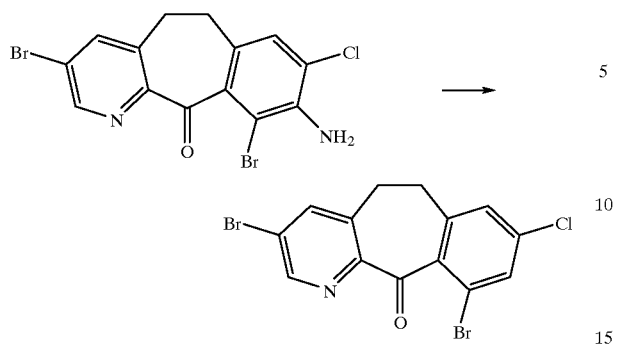

Cool 100 ml of concentrated HCl (aqueous) to 0° C., then add 5.61 g (81.4 mmol) of NaNO$_2$ and stir for 10 min. Slowly add (in portions) 11.3 g (27.1 mmol) of the product of Step C and stir the mixture at 0°–3° C. for 2.25 hrs. Slowly add (dropwise) 180 ml of 50% H$_3$PO$_2$ (aqueous) and allow the mixture to stand at 0° C. overnight. Slowly add (dropwise) 150 ml of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product.

Step E

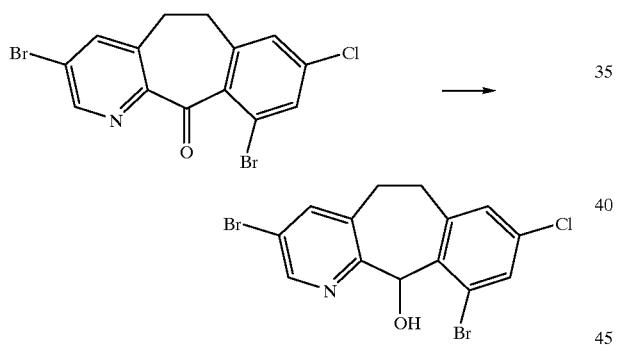

Combine 8.6 g (21.4 mmol) of the product of Step D and 300 ml of MeOH and cool to 0°–2° C. Add 1.21 g (32.1 mmol) of NaBH$_4$ and stir the mixture at ~0° C. 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

Step F

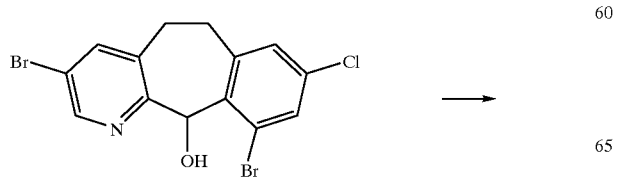

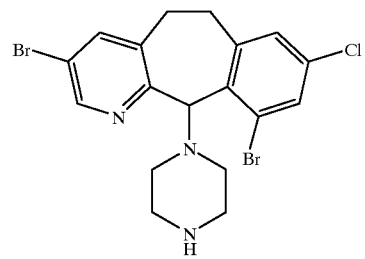

Combine 8.2 g (20.3 mmol) of the product of Step E and 160 ml of CH$_2$Cl$_2$, cool to 0° C., then slowly add (dropwise) 14.8 ml (203 mmol) of SOCl$_2$ over a 30 min. period. Warm the mixture to room temperature and stir for 4.5 hrs., then concentrate in vacuo to a residue, add CH$_2$Cl$_2$ and wash with 1 N NaOH (aqueous) then brine and dry over Na$_2$SO$_4$. Concentrate in vacuo to a residue, then add dry THF and 8.7 g (101 mmol) of piperazine and stir at room temperature overnight. Concentrate in vacuo to a residue, add CH$_2$Cl$_2$, and wash with 0.25 N NaOH (aqueous), water, then brine. Dry over Na$_2$SO$_4$ and concentrate in vacuo to give 9.46 g of the crude product. Chromatograph (silica gel, 5% MeOH/CH$_2$Cl$_2$+NH$_3$) to give 3.59 g of the title compound, as a racemate.

Step G—Separation of Enantiomers

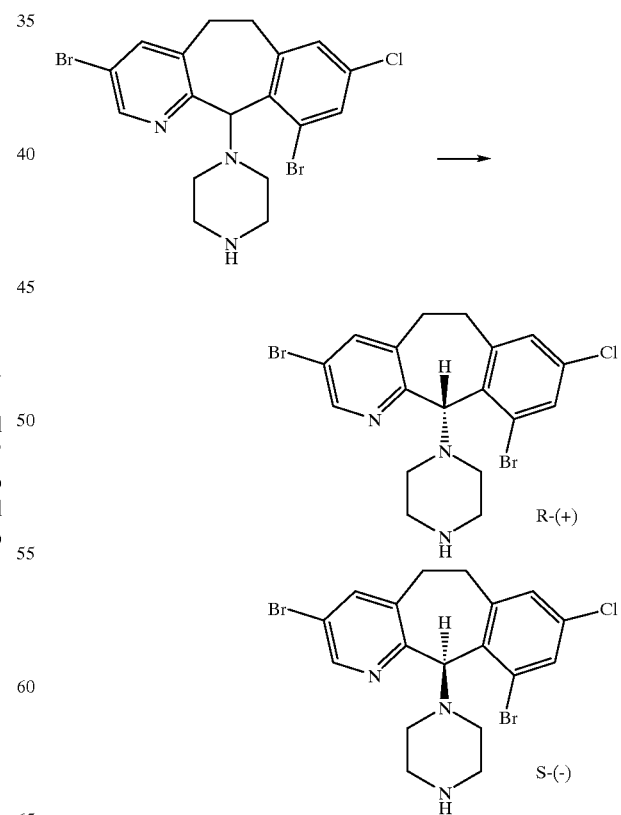

The racemic title compound from Step F (5.7 g) is chromatographed by preparative chiral chromatography (Chiralpack AD, 5 cm×50 cm column, flow rate 100 ml/min) using 30% iPrOH/hexane+0.2% diethylamine, to give 2.88 g of the R-(+)-enantiomer and 2.77 g of the S-(−)-enantiomer of the title compound.

Preparative Example 7

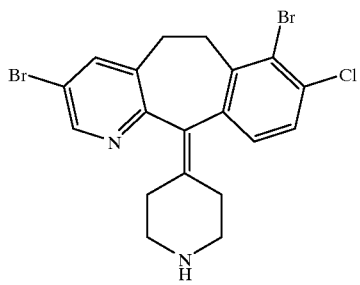

Step A

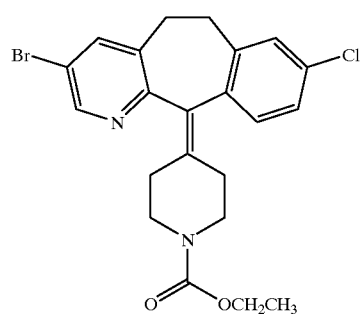

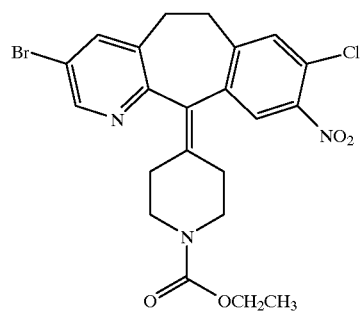

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 ml of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 ml of $CH_2Cl_2$. Wash the extract with 200 ml of water, dry over $MgSO_4$, then filter and concentrate in vacuo to a residue. Chromatograph the residue (silica gel, 10% EtOAc/$CH_2Cl_2$) to give 24.4 g (86% yield) of the product. m.p. =165–167° C.

Step B

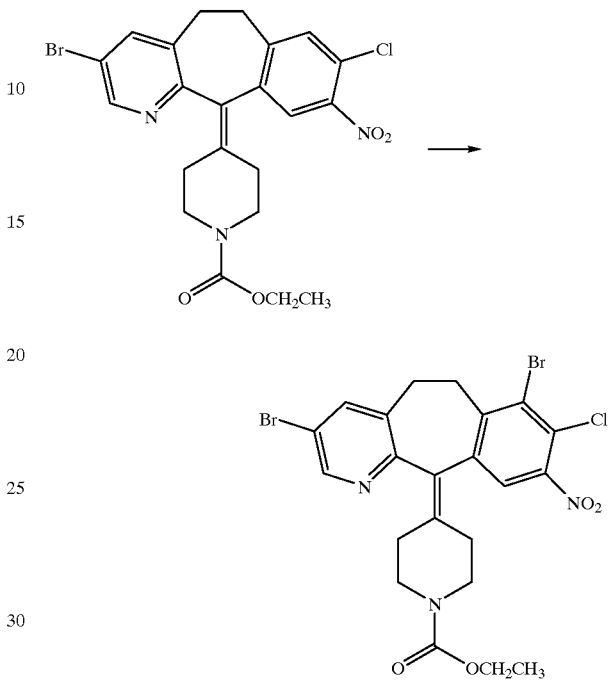

Combine 20 g (40.5 mmol) of the product of Step A and 200 ml of concentrated $H_2SO_4$ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 ml of water, slurry in 200 ml of acetone and filter to provide 19.79 g (85.6% yield) of the product.

Step C

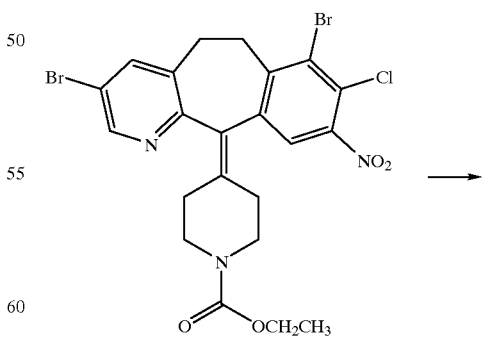

-continued

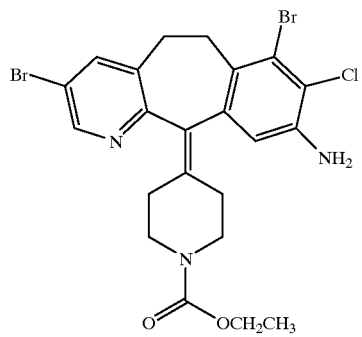

Combine 25 g (447 mmol) of Fe filings, 10 g (90 mmol) of CaCl$_2$ and a suspension of 20 g (34.19 mmol) of the product of Step B in 700 ml of 90:10 EtOH/water at 50° C. Heat the mixture at reflux overnight, filter through Celite® and wash the filter cake with 2×200 ml of hot EtOH. Combine the filtrate and washes, and concentrate in vacuo to a residue. Extract the residue with 600 ml of CH$_2$Cl$_2$, wash with 300 ml of water and dry over MgSO$_4$. Filter and concentrate in vacuo to a residue, then chromatograph (silica gel, 30% EtOAc/CH$_2$Cl$_2$) to give 11.4 g (60% yield) of the product.

Step D

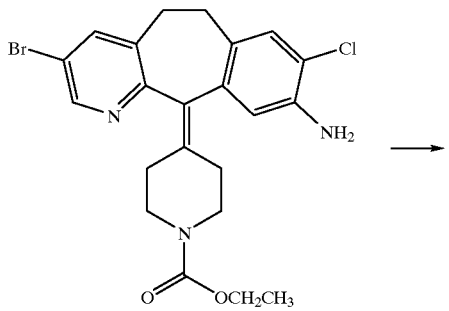

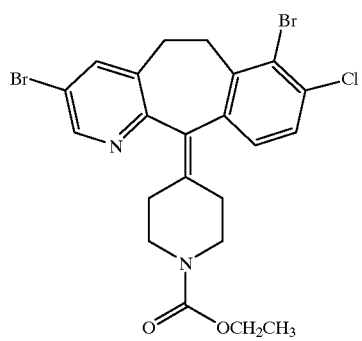

Slowly add (in portions) 20 g (35.9 mmol) of the product of Step C to a solution of 8 g (116 mmol) of NaNO$_2$ in 120 ml of concentrated HCl (aqueous) at −10° C. Stir the resulting mixture at 0° C. for 2 hours, then slowly add (dropwise) 150 ml (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 ml of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product.

Step E

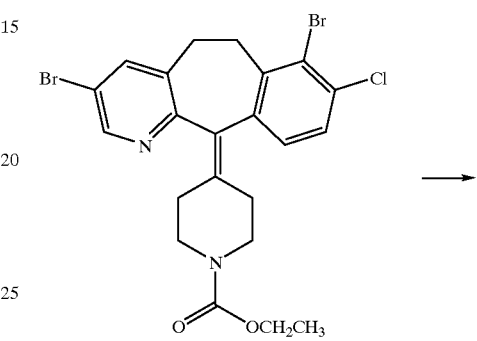

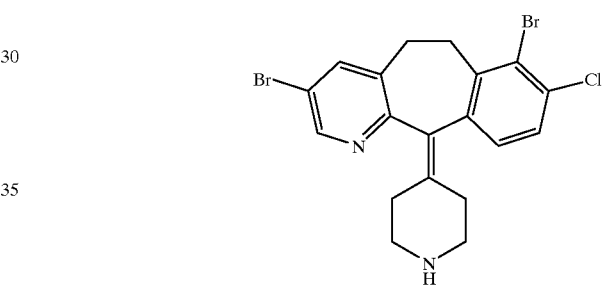

Combine 6.8 g (12.59 mmol) of the product of Step D and 100 ml of concentrated HCl (aqueous) and stir at 85° C. overnight. Cool the mixture, pour it into 300 g of ice and basify with concentrated NH$_4$OH (aqueous). Extract with 2×300 ml of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound.

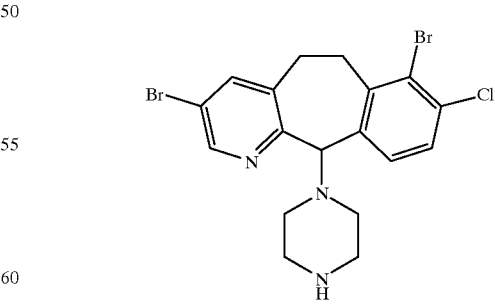

Preparative Example 8

[racemic as well as (+)- and (−)-enantiomers]

Step A

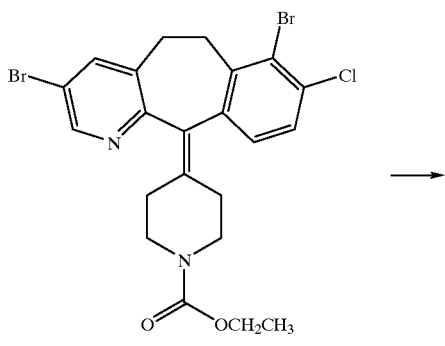

Combine 16.6 g (0.03 mole) of the product of Preparative Example 7, Step D, with a 3:1 solution of CH₃CN and water (212.65 ml CH₃CN and 70.8 ml of water) and stir the resulting slurry overnight at room temperature. Add 32.833 g (0.153 mole) of NaIO₄ and then 0.31 g (2.30 mmol) of RuO₂ and stir at room temperature (the addition of RuO₂ is accompanied by an exothermic reaction and the temperature climbs from 20° to 30° C.). Stir the mixture for 1.3 hrs. (temperature returned to 25° C. after about 30 min.), then filter to remove the solids and wash the solids with CH₂Cl₂. Concentrate the filtrate in vacuo to a residue and dissolve the residue in CH₂Cl₂. Filter to remove insoluble solids and wash the solids with CH₂Cl₂. Wash the filtrate with water, concentrate to a volume of about 200 ml and wash with bleach, then with water. Extract with 6 N HCl (aqueous). Cool the aqueous extract to 0C and slowly add 50% NaOH (aqueous) to adjust to pH=4 while keeping the temperature <30° C. Extract twice with CH₂Cl₂, dry over MgSO₄ and concentrate in vacuo to a residue. Slurry the residue in 20 ml of EtOH and cool to 0° C. Collect the resulting solids by filtration and dry the solids in vacuo to give 7.95 g of the product.

Step B

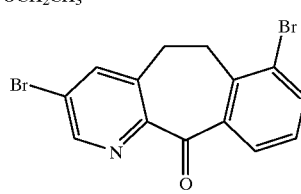

Combine 21.58 g (53.75 mmol) of the product of Step A and 500 ml of an anhydrous 1:1 mixture of EtOH and toluene, add 1.43 g (37.8 mmol) of NaBH₄ and heat the mixture at reflux for 10 min. Cool the mixture to 0° C., add 100 ml of water, then adjust to pH=4–5 with 1 M HCl (aqueous) while keeping the temperature <10° C. Add 250 ml of EtOAc and separate the layers. Wash the organic layer with brine (3×50 ml) then dry over Na₂SO₄. Concentrate in vacuo to a residue (24.01 g) and chromatograph the residue (silica gel, 30% hexane/CH₂Cl₂) to give the product. Impure fractions were purified by rechromatography. A total of 18.57 g of the product is obtained.

Step C

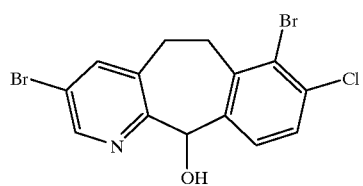

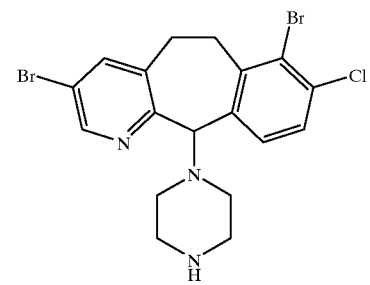

Combine 18.57 g (46.02 mmol) of the product of Step B and 500 ml of CHCl₃, then add 6.70 ml (91.2 mmol) of SOCl₂, and stir the mixture at room temperature for 4 hrs. Add a solution of 35.6 g (0.413 mole) of piperazine in 800 ml of THF over a period of 5 min. and stir the mixture for 1 hr. at room temperature. Heat the mixture at reflux overnight, then cool to room temperature and dilute the mixture with 1 L of CH₂Cl₂. Wash with water (5×200 ml), and extract the aqueous wash with CHCl₃ (3×100 ml). Combine all of the organic solutions, wash with brine (3×200 ml) and dry over MgSO₄. Concentrate in vacuo to a residue and chromatograph (silica gel, gradient of 5%, 7.5%, 10% MeOH/CH₂Cl₂ +NH₄OH) to give 18.49 g of the title compound as a racemic mixture.

Step D—Separation of Enantiomers

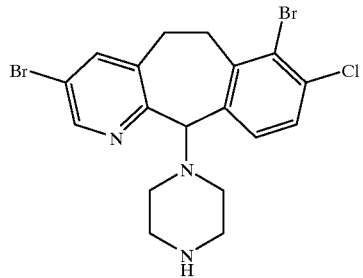

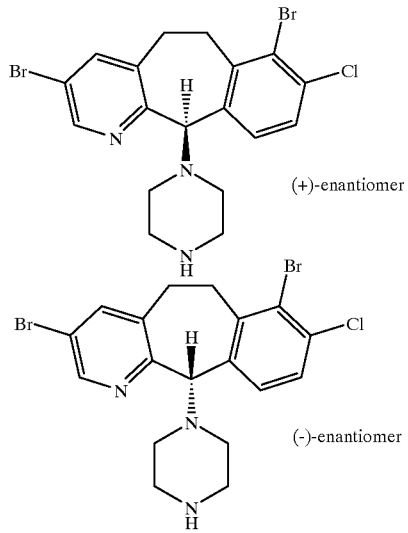

The racemic title compound of Step C is separated by preparative chiral chromatography (Chiralpack AD, 5 cm×50 cm column, flow rate 100 ml/min., 20% iPrOH/hexane+0.2% diethylamine), to give 9.14 g of the (+)-enantiomer and 9.30 g of the (−)-enantiomer.

Preparative Example 9

[racemic as well as (+)- and (−)-enantiomer]

Step A

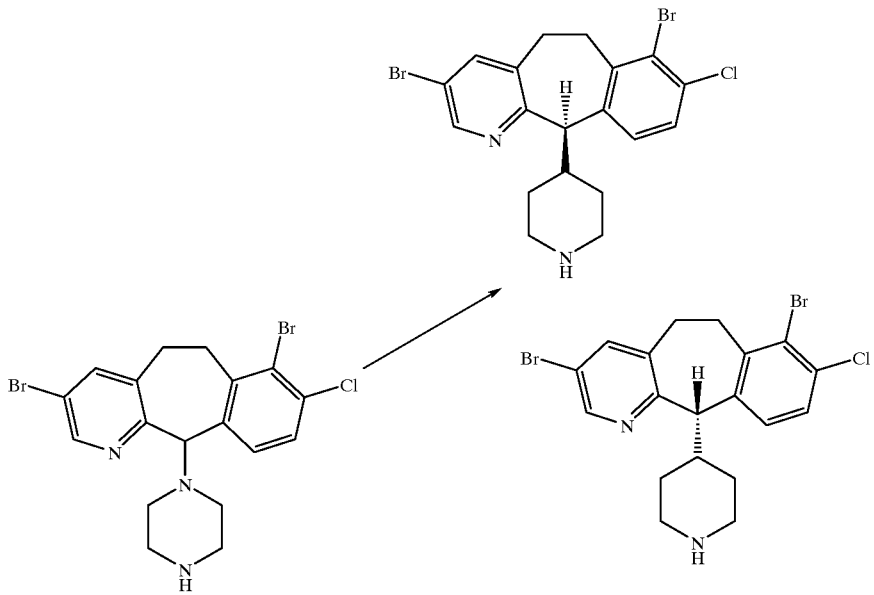

Combine 13 g (33.3 mmol) of the title compound from Preparative Example 7, and 300 ml of toluene at 20° C., then add 32.5 ml (32.5 mmol) of a 1 M solution of DIBAL in toluene. Heat the mixture at reflux for 1 hr., cool to 20° C., add another 32.5 ml of 1 M DIBAL solution and heat at reflux for 1 hr. Cool the mixture to 20° C. and pour it into a mixture of 400 g of ice, 500 ml of EtOAc and 300 ml of 10% NaOH (aqueous). Extract the aqueous layer with $CH_2Cl_2$ (3×200 ml), dry the organic layers over $MgSO_4$, then concentrate in vacuo to a residue. Chromatograph (silica gel, 12% MeOH/$CH_2Cl_2$+4% $NH_4OH$) to give 10.4 g of the title compound as a racemate.

Step B—Separation of Enantiomers

The racemic title compound of Step A is separated by preparative chiral chromatography (Chiralpack AD, 5 cm×50 cm column, using 5% iPrOH/hexane+0.2% diethylamine), to give the (+)-enantiomer and the (−)-enantiomer of the title compound.

Preparative Example 10

1-(3-Bromo-8-chloro-6,11-dihydro-5H-benzo[5,6]cyclohepta[1,2-b]pyridin-11-yl)-4-[(4-piperidinyl)acetyl]piperazine

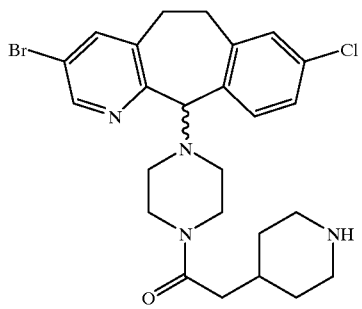

Step A 1,1-Dimethylethyl 4-[[[4-(3-bromo-8-chloro-6,11-dihydro-5H-benzo[5,6]cyclohepta[1,2-b]pyridin-11-YL)-1-piperazinyl]carbonyl]methyl]-1-piperidinecarboxylate

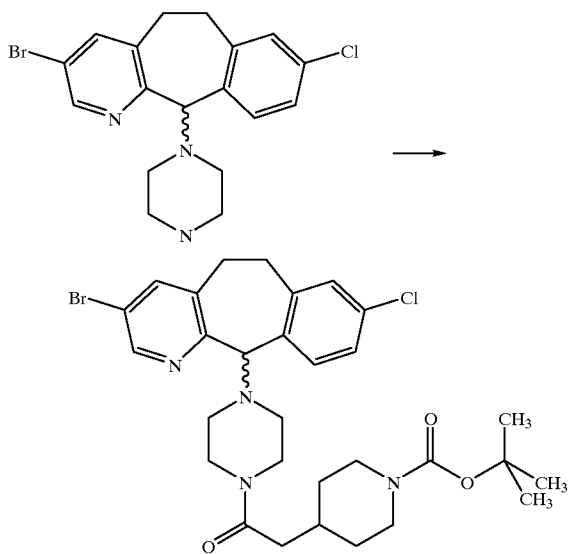

3-Bromo-8-chloro-6,11-dihydro-11-(1-piperazinyl)-5H-benzo[5,6]cyclohepta[1,2-b]pyridine (3 g, 7.6 mmoles), 1-N-tert-butoxycarbonylpiperidinyl-4-acetic acid (2.42 g, 9.9 mmoles), 1-(3-dimethylaminopropyl)-3-ethylcarbodiimide hydrochloride (1.9 g, 9.9 mmoles), 1-hydroxybenzotriazole (1.34 g, 9.9 mmoles) and 4-methylmorpholine (1.092 ml, 9.9 mmoles) were dissolved in anhydrous DMF (100 ml) and the mixture was stirred at 25° C. under argon for 24 h. The solution was evaporated to dryness and the residue was taken up in dichloromethane and washed with saturated aqueous sodium bicarbonate, water and then dried over $MgSO_4$. The mixture was filtered and evaporated to dryness. Chromatography on silica gel using 2% (10% conc. $NH_4OH$ in methanol)dichloromethane as the eluant afforded the title compound (Yield: 4.72 g; 100%).

Step B 1-(3-bromo-8-chloro-6,11-dihydro-5H-benzo[5,6]cyclohepta[1,2-b]pyridin-11-yl)-4-[(4-piperidinyl)acetyl]piperazine

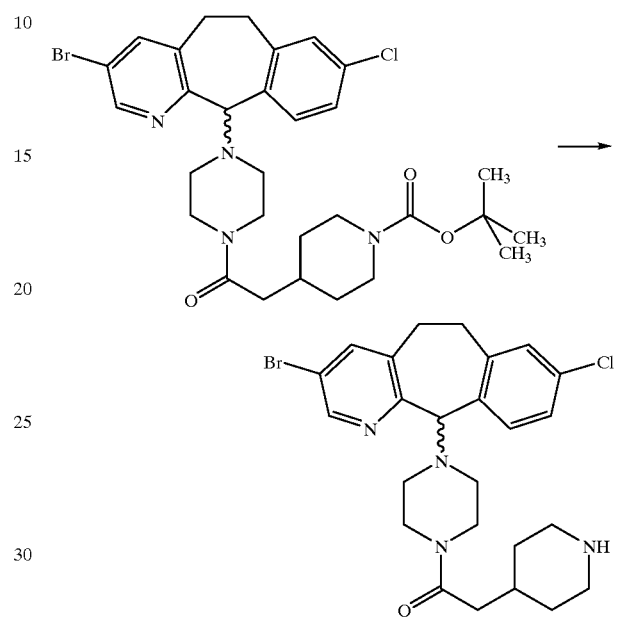

The title compound from Step A above (4.61 g) (7.5 mmoles) was dissolved in methanol (40 ml) and a 10% (v/v) conc. $H_2SO_4$ in dioxane solution (100 ml) was added. The mixture was stirred at 25° C. for 2 h and then basified with conc. aqueous NaOH. The mixture was extracted with dichloromethane and the latter was washed with water, dried over $MgSO_4$, filtered and evaporated to dryness. The product was chromatographed on silica gel using 10% (10% conc. $NH_4OH$ in methanol)dichloromethane as the eluant to give the title compound (Yield: 2.86 g; 74%).

ASSAYS

1. In vitro enzyme assays: FPT $IC_{50}$ (inhibition of farnesyl protein tranferase, in vitro enzyme assay) are determined by the methods disclosed in WO/10515 or WO 95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<10 μM) inhibitors of Ras-CVLS farnesylation by partially purified rat brain FPT.

2. Cell-based assay. COS $IC_{50}$ values refer to the COS cells activity inhibition of Ras processing, are determined by the methods disclosed in WO/10515 or WO 95/10516.

| Example | FPT $IC_{50}$ (μM) | COS Cell $IC_{50}$ (μM) |
|---|---|---|
| 1 | 0.0051 | 0.0500 |
| 2 | 0.0054 | 0.0330 |
| 3 | 0.0019 | 0.0085 |

-continued

| Example | FPT IC$_{50}$ ($\mu$M) | COS Cell IC$_{50}$ ($\mu$M) |
|---|---|---|
| 4 | 0.0020 | 0.0220 |
| 5 | 0.0050 | 0.1500 |
| 6 | 0.0017 | 0.0200 |
| 7 | 0.0038 | 0.0180 |
| 8 | 0.0087 | 0.1200 |
| 9 | 0.0033 | 0.1100 |
| 10 | 0.0046 | 0.3000 |
| 11 | 0.0031 | 0.0180 |
| 12 | 0.0008 | 0.3600 |
| 13 | 0.0009 | 0.0250 |
| 14 | 0.0500 | 0.7500 |
| 15 | 0.1000 | 1.5000 |
| 16 | 0.1080 | — |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

Example A—Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B—Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

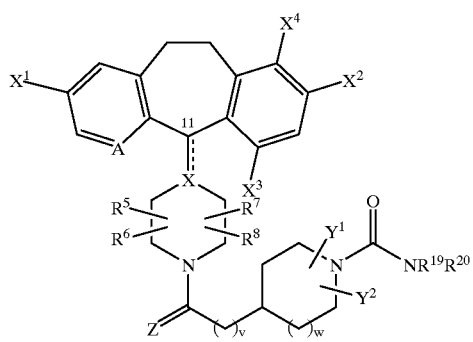

(1.0)

or a pharmaceutically acceptable salt or solvate thereof, wherein:

A represents N or N-oxide;

X represents CH or C, such that when X is CH, there is a single bond to carbon atom 11 as represented by the solid line; or when X is C, there is a double bond to carbon atom 11, as represented by the solid and dotted lines;

$X^1$ and $X^2$ are independently selected from bromo or chloro, and $X^3$ and $X^4$ are independently selected from hydrogen, bromo or chloro provided that at least one of $X^3$ and $X^4$ is hydrogen;

$Y^1$ and $Y^2$ are independently selected from hydrogen or alkyl;

Z is =O or =S;

$R^5$, $R^6$, $R^7$ and $R^8$ each independently represents hydrogen, —$CF_3$, alkyl or aryl, and further wherein $R^5$ may be combined with $R^6$ to represent =O or =S and/or $R^7$ may be combined with $R^8$ to represent =O or =S;

$R^{19}$ and $R^{20}$ are selected from: hydrogen, alkoxy, aryl, aralkyl, heteroaryl, heteroarylalkyl, cycloalkyl, cycloalkylalkyl, heterocycloalkyl or heterocycloalkylalkyl, with the proviso that $R^{19}$ and $R^{20}$ are not both hydrogen;

v is zero, 1, 2 or 3; and w is zero or 1.

2. The compound of claim 1 wherein there is a single bond at carbon atom 11, X is CH, Z is =O and $R^5$, $R^6$, $R^7$ and $R^8$ are hydrogen.

3. The compound of claim 2 wherein $X^1$ is bromo, $X^2$ is chloro, $X^3$ is bromo and $X^4$ is hydrogen.

4. The compound of claim 3 wherein Z is =O; v is 1, w is 1, and $Y^1$ and $Y^2$ are hydrogen.

5. The compound of claim 4 wherein $R^{19}$ a nd $R^{20}$ are independently selected from hydrogen, aryl and heterocycloalkyl wit h the proviso that $R^{19}$ and $R^{20}$ are not both hydrogen.

6. The compound of claim 5 wherein; the aryl group is substituted with alkoxy; and the heterocycloalkyl group is substituted with —$COOR^{10}$ wherein $R^{10}$ is hydrogen or alkyl.

7. The compound of claim 1 wherein there is a single bond at carbon atom 11, X is CH, Z is =O, $R^5$, $R^6$, $R^7$ and $R^8$ are hydrogen, $X^1$ is bromo, $X^2$ is chloro, $X^3$ is bromo and $X^4$ is hydrogen, v is 1, w is 1, and $Y^1$ and $Y^2$ are hydrogen, $R^{19}$ and $R^{20}$ are independently selected from hydrogen, aryl and heterocycloalkyl; wherein the aryl group is substituted with alkoxy; and the heterocycloalkyl group is substituted with —$COOR^{10}$ wherein $R^{10}$ is hydrogen or alkyl, with the proviso that $R^{19}$ and $R^{20}$ are not both hydrogen.

8. A compound selected from the group consisting of:

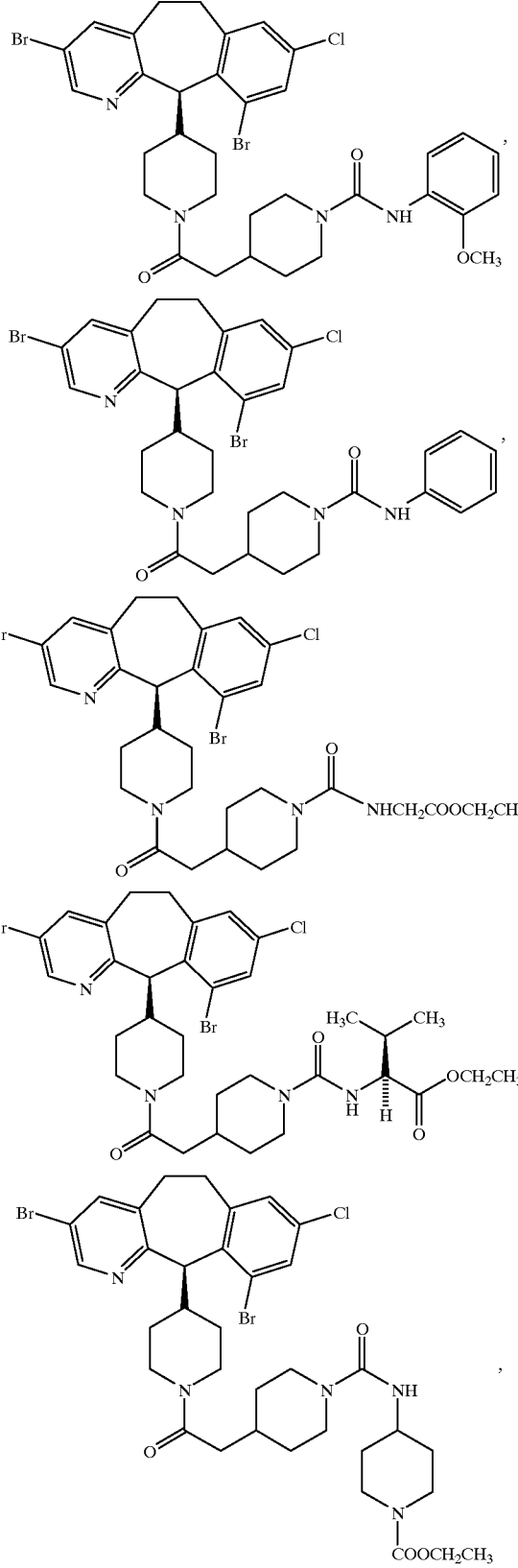

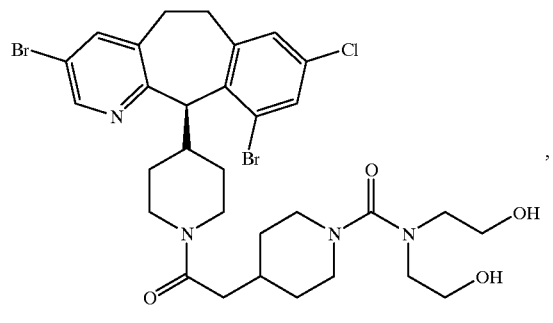
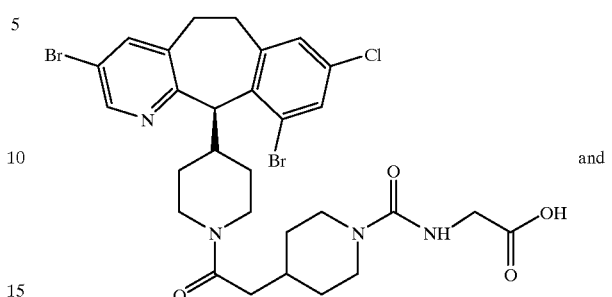
and
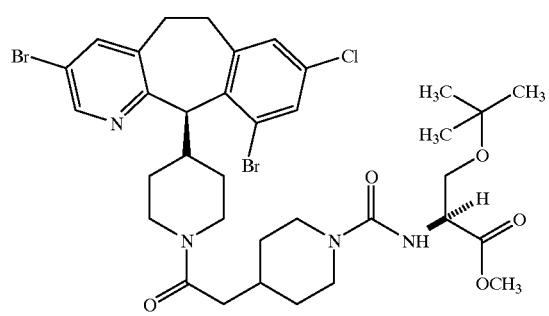
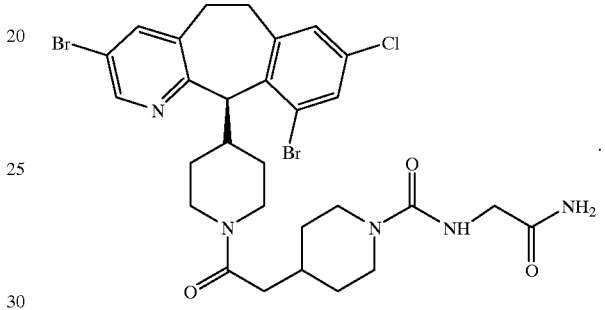
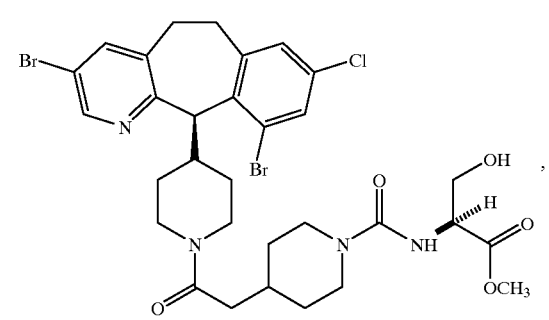
9. A compound selected from the group consisting of:
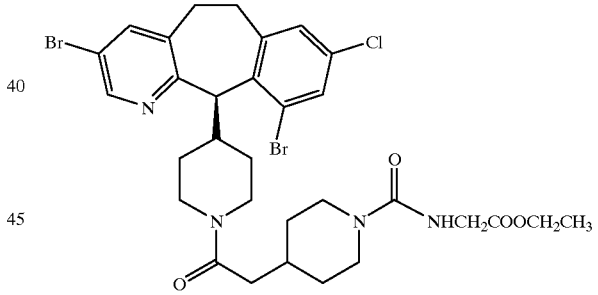
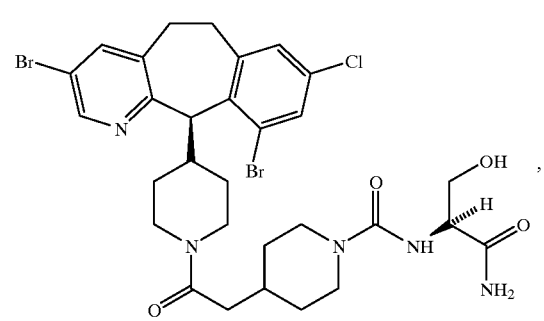
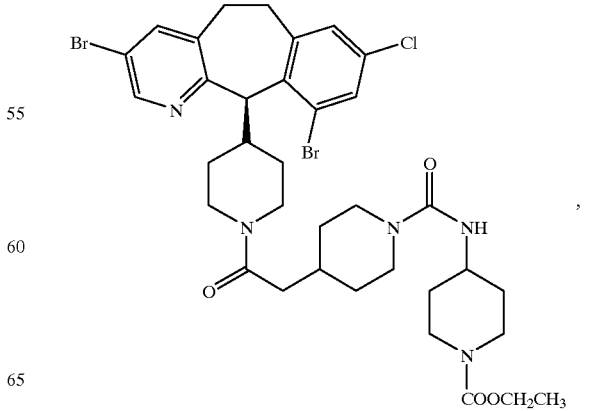

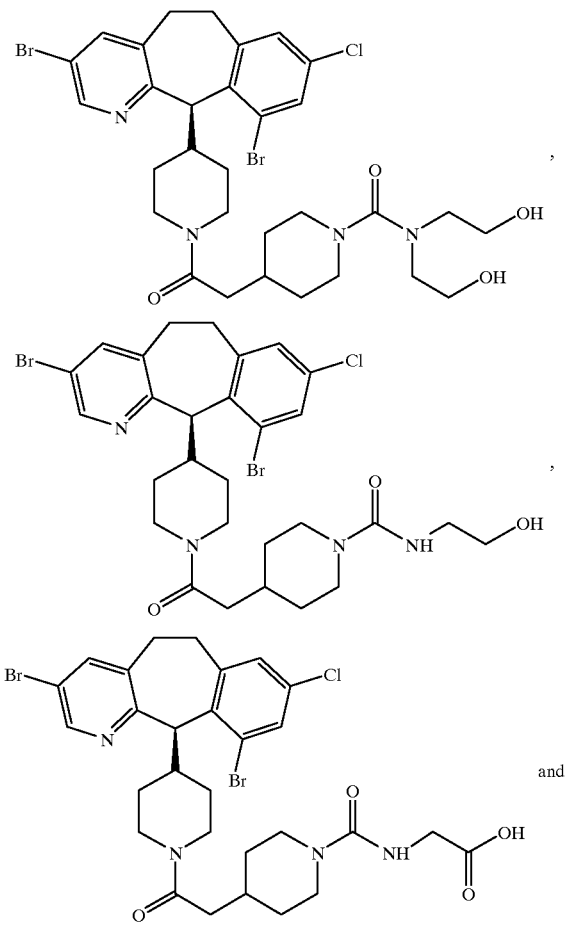

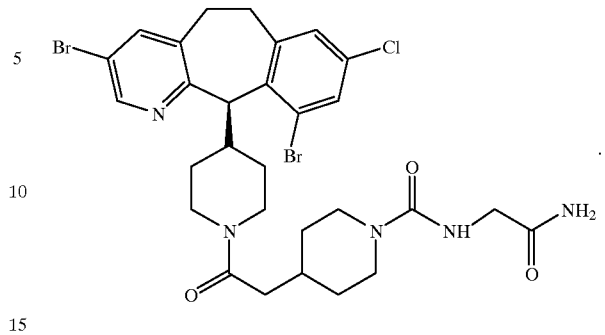

10. A pharmaceutical composition comprising an effective amount of compound of claim 1 in combination with a pharmaceutically acceptable carrier.

11. A method of inhibiting farnesyl protien transferase in tumor cells expressing an activated ras oncogene comprising administering to a human in need thereof, a farnesyl protein transferase inhibiting amount of a compound of claim 1.

12. The method of claim 11 wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, prostate tumor cells, breast tumor cells or colon tumors cells.

13. A method of inhibiting farnesyl protein transferase comprising administering an effective amount of a compound of claim 1 to a human in need thereof.

* * * * *